US006863886B2

(12) United States Patent
Karageozian et al.

(10) Patent No.: US 6,863,886 B2
(45) Date of Patent: Mar. 8, 2005

(54) USE OF HYALURONIDASE IN THE MANUFACTURE OF AN OPHTHALMIC PREPARATION FOR LIQUEFYING VITREOUS HUMOR IN THE TREATMENT OF EYE DISORDERS

(75) Inventors: Hampar Karageozian, San Juan Capistrano, CA (US); Vicken Karageozian, San Juan Capistrano, CA (US); Maria C. Kenney, Malibu, CA (US); Jose L. G. Flores, Colonia Leyva Aleman (MX); Gabriel Arturo Carpio Aragon, Col. Aviacion (MX); Anthony B. Nesburn, Malibu, CA (US)

(73) Assignee: Advanced Corneal Systems, Irvine, CA (US)

( * ) Notice: Subject to any disclaimer, the term of this patent is extended or adjusted under 35 U.S.C. 154(b) by 0 days.

(21) Appl. No.: 10/371,850

(22) Filed: Feb. 21, 2003

(65) Prior Publication Data

US 2003/0170224 A1 Sep. 11, 2003

Related U.S. Application Data

(63) Continuation of application No. 09/444,003, filed on Nov. 19, 1999, now Pat. No. 6,610,292, which is a continuation of application No. PCT/US98/10578, filed on May 22, 1998, which is a continuation-in-part of application No. 08/862,620, filed on May 22, 1997, now abandoned, which is a continuation-in-part of application No. 08/561,623, filed on Nov. 22, 1995, now Pat. No. 5,866,120.

(51) Int. Cl.$^7$ .............................................. A61K 38/43

(52) U.S. Cl. ................ 424/94.62; 424/94.1; 424/94.61; 424/94.63; 424/94.64; 424/94.67; 424/601; 526/123.13; 514/912

(58) Field of Search ............................ 424/94.62, 94.1; 435/183, 201

(56) References Cited

U.S. PATENT DOCUMENTS

| 3,728,223 A | 4/1973 | Kaneko et al. |
| 3,869,548 A | 3/1975 | Dabis |
| 3,945,889 A | 3/1976 | Mima et al. |

(List continued on next page.)

FOREIGN PATENT DOCUMENTS

| EP | 0 193 330 A2 | 9/1986 |
| EP | 0625579 B1 | 11/1994 |
| EP | 0892045 A3 | 1/1999 |
| EP | 1048725 A1 | 11/2000 |
| WO | WO 97/18835 | 5/1997 |
| WO | WO 00/77221 | 12/2000 |

OTHER PUBLICATIONS

Anloszyk, et al., "An Experimental Model of Preretinal Neovascularization in the Rabbit" Investigative Ophthalmology & Visual Science, 32 : 46–52 (1991).

Belkin, et al., "Urokinase–Treatment of Fresh Laser Irradiation–Induced Vitreous Hemorrhage", Ophthalmologica, Basel, 187 : 152–156 (1983).

(List continued on next page.)

Primary Examiner—Patricia Leith
(74) Attorney, Agent, or Firm—Knobbe, Martens, Olson & Bear, LLP

(57) ABSTRACT

An enzymatic method is provided for treating ophthalmic disorders of the mammalian eye. Prevention of neovascularization and the increased rate of clearance from the vitreous of materials toxic to retina is accomplished by administering an amount of hyaluronidase effective to liquefy the vitreous humor of the treated eye without causing toxic damage to the eye. Liquefaction of the vitreous humor increases the rate of liquid exchange from the vitreal chamber. This increase in exchange removes those materials and conditions whose presence causes ophthalmological and retinal damage.

20 Claims, 6 Drawing Sheets

U.S. PATENT DOCUMENTS

| | | | |
|---|---|---|---|
| 4,141,973 A | 2/1979 | Balazs |
| 4,174,389 A | 11/1979 | Cope |
| 4,258,134 A | 3/1981 | Yoshida et al. |
| 4,474,751 A | 10/1984 | Haslam et al. |
| 4,490,351 A | 12/1984 | Clark, Jr. |
| 4,757,089 A | 7/1988 | Epstein |
| 4,820,516 A | 4/1989 | Sawyer et al. |
| 4,861,760 A | 8/1989 | Mazuel et al. |
| 4,871,742 A | 10/1989 | Bonne et al. |
| 4,897,349 A | 1/1990 | Swann et al. |
| 4,904,594 A | 2/1990 | Karlstam |
| 5,061,627 A | 10/1991 | Olsen et al. |
| 5,077,033 A | 12/1991 | Viegas et al. |
| 5,166,331 A | 11/1992 | Della Valle et al. |
| 5,252,318 A | 10/1993 | Joshi et al. |
| 5,260,059 A | 11/1993 | Acott et al. |
| 5,270,051 A | 12/1993 | Harris |
| 5,292,509 A | 3/1994 | Hageman |
| 5,300,295 A | 4/1994 | Viegas et al. |
| 5,316,926 A | 5/1994 | Brown et al. |
| 5,318,780 A | 6/1994 | Viegas et al. |
| 5,326,761 A | 7/1994 | Rozier |
| 5,366,964 A | 11/1994 | Lindstrom et al. |
| 5,496,726 A | 3/1996 | Park et al. |
| 5,593,877 A | 1/1997 | King |
| 5,747,027 A | 5/1998 | Stern et al. |
| 5,756,552 A | 5/1998 | Takeuchi et al. |
| 5,827,721 A | 10/1998 | Stern et al. |
| 5,866,120 A | 2/1999 | Karageozian et al. |
| 6,039,943 A | 3/2000 | Karageozian et al. |
| 6,123,938 A | 9/2000 | Stern et al. |
| RE37,336 E | 8/2001 | Weigel et al. |
| 6,551,590 B2 * | 4/2003 | Karageozian et al. |
| 6,610,292 B2 * | 8/2003 | Karageozian et al. |

OTHER PUBLICATIONS

Benson, et al. (1971) *Vitreous Hemorrhage*. Survey of Ophthalmology 5:297–311.

Biozyme Laboratories web page: http://www.biozyme.com/p38.html.

Boyer, et al. (1958) *Studies on Simulated Vitreous Hemorrhages*. A.M.A. Archives of Ophthalmology 59:333–338.

Borowski, et al. "Influence of Hyaluronidaze on Vitreous Haemorrhages", Klin. Oczna 87: 129–30 (1985).

Bramsen, T., "The Effect of Urokinase on Central Corneal Thickness and Vitreous Haemorrhage", Acta Ophthalmologica, 56 1006–1012 (1978).

Calbiochem 1994/95, CATALOG 1994/95 (6 pages).

Chapman–Smith, et al., "Urokinase in the Management of Vitreous Haemorrhage", British Journal of Ophthalmology, 61 : 500–505 (1977).

Cleary,e t al., "Intravitreal Urokinase in the Treatment of Vitreous Hemorrhage", Transactions of the Ophthalmological Societies of the United Kingdom, 94 : 587–590 (1974).

Coleman, et al., "The Role of Vitrectomy in Traumatic Vitreopathy", Symposium: Pars Plana Vitrectomy, 81 :OP 406–OP413, (1976).

Coles, et al., "Vitrectomy in Intraocular Trauma", Archives ofOphthamology, 87 : 621–628 (1972).

Constable, et al., "Pathology of Vitreous Membranes and the Effect of Hemmorrhage and New Vessels on the Vitreous", Transactions of the Ophthalmological Societies of the United Kingdom, 95 : 382–388 (1975).

Dugmore, et al., "Intravitreal Urokinase in the Treatment of Vitreous Hemmorrhage", American Journal of Ophthalmology, 75 : 779–781 (1973).

Singh, Daljit, (1995) "Subconjunctival Hyaluronidase Injection Producing Temporary Myopia," *Journal of Cateract & Refractive Surgery*, vol. 21, pp. 477–478.

Yee et al., (1994) "Treatment With Streptokinase in Experimental Penetrating Keratoplasty in Rabbits," *Investigative Ophthalmology & Visual Science*, vol. 35, p. 1878.

"Enzyme Nomenclature–Enzyme List", International Union of Biochemistry and Molecular Biology, prepared for NC–IUBMB by Edwin C. Webb, pp. 350, (1992).

Forrester, et al., "Resolutions of Intravitreal Clots by Urokinase", LANCET, 2 : 179 (1973b).

Forrester, et al., "Lytic Therapy in Vitreous Hemorrhage", Transactions of the Ophthalmological Societies of the United Kingdom, 94 : 582–588 (1974).

Forrester, et al., "Total Vitreous Haemorrhage A Method of Treatment, "Transactions of the Ophthmological Societies of the United Kingdom, 94 : 992–999 (1974).

Forrester, et al., "Intravitreal Fibrinolysis on Experimental Vitreous Hemorrhage", Experimental Eye Research, 22 : 181–188 (1976).

Forrester, et al., "The Effect of Fibrinolytic Inhibition in the Resolution of Experimental Vitreous Haemorrhage", American Journal of Ophthalmology, 84 : 810–814 (1977).

Forrester, et al., "The Pathology of Vitreous Hemorrhage. I Gross and Histological Appearances", Archives of Ophthalmology, 90 : 703–710 (1978).

Forrester, et al., "The Pathology of Vitreous Hemorrhage, II. Ultrastructure", Archives of Ophthalmology, 57 : 2368–2374 (1979).

Foulds, et al., Effect of Intravitreal Hyalruondise on the Clearance of Triliated Water from the Vitreous to the Choroid British Journal of Ophthalmology, 69 : 529–532 (1985).

Ghartey, et al., "Closed Vitreous Surgery, XVII. Results and Complications of Pars Plana Vitrectomy", Archives of Ophthalmology, 98 : 1248–1252 (1980).

Gibbons, et al., "Retinal Damage from Suprathreshold Q–switch Laser Exposure", Health Physics, 35 : 461–469 (1978).

Gottlieb, et al., "The Safety of Intravitreal Hyaluronidase", Investigative Ophthalmology Visual Science, 31 :2345–2352 (1990).

Greer, et al., "A Study of Stimulated Vitreous Hemorrahge Using Labeled Blood", Archives of Ophthalmology, 79 : 755–758 (1968).

Hageman, et al., "Chrondroitin 6–Sulfate Glycosaminoglycan is a Major Constituent of Primate Cone Photoreceptor Matrix Sheaths", Dept. of Anatomy and Cell Biology, Univ. of Southern California School of Medicine, Los Angeles, Current Eye Research, 6 : 639–646 (1987).

Harooni, et al. (1998) *Efficacy and Safety of Enzymatic Posterior Vitreous Detachment by Intravitreal Injection of Hyaluronidase*. Retina 18:116–22.

Harooni, et al. (1996) *Efficacy and Safety of Vitreous Liquefaction by Intravitreal Injection of Hyaluronidase*. Abstract: Investigative Ophthalmology and Visual Science, Annual Meeting Fort Lauderdale, FL. Apr. 21, through Apr. 26, 1996.

Holmes,e t al., "Intravitreal Urokinase in the Management of Vitreous Haemorrhage", Transcript of Ophthalmological Societies of the United Kingdom, 94 : 591–596 (1974).

Kang, et al. (1995) *Induction of Bitreolysis and Vitreous Detachment with Hyaluronidase and Perfluoroproopane Gas*. Korean J. Ophthalmol. 9:69–78.

Karageozian, et al., "Hyaluronidase in intravireal use; evaluation of toxicity in animal model", Investigative Opthmalmology & Visual Science, 38(4), abstract XP002076958, (May 15, 1997).

Kim, et al., "The Influence of Enzymes and Inflammation on Absorption of Experimentally Induced Vitreous Hemorrhage", Dept. of Ophthalmology, Korea Univ. Medical Journal, 9(1) : 87–97 (1972).

Knepper, et al. (1984) *Exogenous Hyaluronidases and Degradation of Hyaluronic Acid in the Rabbit Eye*. Investigative Ophthalmology & Visual Science 25:286–293.

Koziol, et al., "Urokinase in Experimental Vitreous Hemorrhage", Ophthalmic Surgery, 6 : 79–82 (1975).

LaNauze, et al. (1982) *Chemotaxis in Vitreous Hemorrhage: An Experimental Study*, Exp. Eye Res. 34:803–813.

Linder, et al., "Hyaluronidase Activity in Cultures of an Anaerobic Strain of Corynebacteria and Some Properties of the Enzyme", Scand. J. Dent. Res., 79 : 523–527 (1971).

Long, C., "Data on Individual Enzymes", Biochemists' Handbook, Van Nostrand, pp. 242–243. (1988).

Maberley, et al. (1970) *The Effect of a Fibrinolytic Agent on Vitreous Hemorrhage in Rabbits*, Canad. J. Ophthal. 5:55–63.

Maberley, et al., "The Effect of a Fibrinolytic Agent on Vitreous Hemorrhage in Rabbits", Canadian Journal of Ophthalmology, 5 : 55–63 (1970).

Machemer, et al., "Experimental Retinal Detachment in the Owl Monkey", American Journal of Ophthalmology 66(3): 388–427 (1968).

Machemer, et al., "A New Concept for Vitreous Surgery, Indications and Results", American Journal of Ophthalmology, 74 : 1034–1056.

Machemer, et al., "Pars Plana Vitrectomy", Transactions of the American Academy of Ophthalmology and Otolaryngology, 81 : 350–351 (1976).

Mandelcorn, et al., "Pars Plana Vitrectomy for the Management of Severe Diabetic Retinopathy", American Journal of Ophthalmology, 81: 561–570 (1976).

Meyer K. et al, "The Enzymes", vol. 4, $2^{nd}$ Ed, pp. 447–460, Academic Press, Inc., New York (1960).

O'Neil, et al., :The Effects of Bacterial Collagenase in Rabbit Vitreous, Canad. J. Ophthal., 8: 366–370 (1973).

Peterson, et al., "Hyaluronidase Effects on Aqueous Outflow Resistance", American Journal of Ophthalmology, 77 (4): 573–577 (1974).

Peyman, et al., "One Hundred Consecutive Pars Plana Vitrectomies Using the Vitrophage", American Journal of Ophthalmology, 81 : 263–271 (1976).

Pierse, et al., "Urokinase in Ophthalmology", LANCET, 2 : 1143–1144 (1963).

Pierse, et al., "The Use of Urokinase in the Anterior Chamber of the Eye", Journal of Clinical Pathology, 17 : 362 (1964).

PDR 43 Edition 1989, Physician's Desk Reference, 2389–2390.

Pirie (1949) *The Effect of Hyaluronidase Injection on The Vitreous Humour of the Rabbit*. British J. Ophthal. 1949:678–684.

Regnault (1970) *Vitreous Hemorrhage: An Experimental Study*. Arch. Ophthal. 83:458–465.

Rietschel, et al., "Ocular Inflammation in Patients Using Soft Contact Lenses", Arch Dermatol., 118 : 147–149 (1982).

Rakusin, et al., "Urokinase in the Treatment of Traumatic Hyphaema", British Journal of Ophthalmology, 55 : 826–832 (1971).

Schimek, et al. (1954) *Vitreous Hemorrhage Absorption—Experimental Study on Rabbit Eyes of the Effects of Intravitreal Hyaluronidase and Streptokinase–Streptodomase and on the Influence of ACTH and Cortisone*. Arch. Ophthal. 82:677–683.

Sigma, pp. 540–541, "Biochemicals Organic Compounds—Diagnostic Reagents", (1990).

Skrzypczak–Spak, et al., "Experimental Liquification of the Vitreous Body", Annals of Ophthalmology, 3(6) :624–630 (1971).

Skrzypczak–Spak, et al. (1971) *Experimental Liquefaction of the Vitreous Body*. Annals of Ophthalmology 3(6):624–630.

Stern, et al. (1992) *An ELISA–Like Assay for Hyaluronidase and Hyaluronidase Inhibitors*. Matrix 12:397–403.

Tanaka, et al. (1996) *Efficacy of Hyaluronidase to Liquefy Vitreous and to Facilitate the Clearance of Vitreous Hemmorrhage*.

Tow, et al., "Urokinase in Pulmonary Embolism", New England Journal of Medicine, 277 : 1161–1167, (1987).

Treister, et al. (1969) *The Effect of Subconjunctivally Injected Hyaluronidase on Corneal Refraction*. Arch Ophthal, 81:645–649.

Twining, et al. (1984) *Acid Proteases of Vitreal Macrophages*. 3(8):1055–1062.

Vercruyase, et al. (1994) *Kinetic Investigation of the Degradation of Hyaluronan by Hyaluronidase using gel Permeation Chromatography*. J. Chromatogr. B 656:179–190.

Williamson, et al., "Urokinase in the Treatment of Vitreous Haemorrhage", LANCET, 2 : 488 (1972).

Williamson, et al., "Treatment of Vitreous Haemorrhage with Urokinase", LANCET, 1 : 888 (1973a).

Winkler, et al., "Hyaluronidase and Retinal Function", Arch Ophthalmol., 103 : 1743–1746 (1985).

\* cited by examiner

FIG. 2

| Hyaluronidase Preparation | SPECIFIC ENZYMATIC ACTIVITIES DETERMINED BY ZYMOGRAPHY | | |
|---|---|---|---|
| | Hyaluronic acid | Gelatin | Casein |
| Hyaluronidase (ACS) | Inactive above 100,000MW | Inactive between 60,000-100,000MW | Inactive above 45,000MW |
| Bovine Hyaluronidase Type VI-S (Sigma) | Active above 100,000MW | Active between 60,000-100,000MW | Active above 45,000MW |
| Ovine Hyaluronidase Type V (Sigma) | Active above 100,000MW | Active between 60,000-100,000MW | Active above 45,000MW |
| Bovine Hyaluronidase Type IV-S | Active above 100,000MW | Active between 60,000-100,000MW | Active above 45,000MW |
| Bovine Hyaluronidase Type I-S | Active above 100,000MW | Active between 60,000-100,000MW | Active above 45,000MW |

FIG. 3

Toxic Effect of Single Dose Intravitreal Injection of BSS, BSS + Thimerisol Hyaluronidase (ACS) and Hyaluronidase (Wydase®) in Rabbits

| Group | Treatment and Dosage (Volume = 100μL) | Results by Day 7 | |
|---|---|---|---|
| | | Fundus Photography Fluorescien Angiography | Histology |
| 1 | BSS | Normal | Normal |
| 2 | BSS + Thimerisol (0.0075mg) | Breakdown of blood - retinal barrier | Retinal necrosis |
| 3 | BSS + (0.025mg) | Severe retinal effects and intravitreal hemorrhage | Severe retinal necrosis |
| 4 | Hyaluronidase (Wydase) - 1 IU | Slight fluorescien leakage. Compromised blood - retinal barrier | No significant change |
| 5 | Hyaluronidase (Wydase) - 15 IU | Severe retinal damage | Equivocal changes |
| 6 | Hyaluronidase (Wydase) - 30 IU | Severe retinal damage | Retinal necrosis |
| 7 | Hyaluronidase (Wydase) - 50 IU | Extensive retinal damage and retinal detachment | Retinal necrosis |
| 8 | Hyaluronidase (Wydase) - 150 IU | Extensive retinal damage and retinal detachment | Severe retinal necrosis |
| 9 | Hyaluronidase (ACS) - 1 IU | Normal | Normal |
| 10 | Hyaluronidase (ACS) - 15 IU | Normal | Normal |
| 11 | Hyaluronidase (ACS) - 30 IU | Normal | Normal |
| 12 | Hyaluronidase (ACS) - 50 IU | Normal | Normal |
| 13 | Hyaluronidase (ACS) - 150 IU | Compromised blood - retinal barrier | Normal |

FIG. 4

Hemorrhage clearing Efficacy of Single - Dose Intravitreal Hyaluronidase (ACS) in the Rabbits
*12 New Zealand Rabbits Are Injected With 10μl or 100μl of blood in both Eyes Intravitreally

|  | Number of Rabbits | Eye Treatments | | Results | |
|---|---|---|---|---|---|
| Group | | Left Eye | Right Eye | Left Eye | Right Eye |
| Group A | 3 | None | 30μl of B.S.S. | Hazy Vitreous Large fibrous Clot | Hazy Vitreous Large fibrous Clot |
| Group B | 3 | None | Hyaluronidase (ACS) 25 I.U. IN 30μL | Hazy Vitreous Large fibrous Clot | Clear vitreous |
| Group C | 3 | None | Hyaluronidase (ACS) 50 I.U. IN 30μL | Hazy Vitreous Large fibrous Clot | Clear vitreous |
| Group D | 3 | None | Hyaluronidase (ACS) 75 I.U. IN 30μL | Hazy Vitreous Large fibrous Clot | Clear vitreous |

FIG. 5

Safety and Efficacy of Multiple - Dose Intravitreal Hyaluronidase (ACS) in Rabbit Eyes

| Group | Number of Rabbits | Eye Treatments | | Results | |
|---|---|---|---|---|---|
| | | Left Eye | Right Eye | Left Eye | Right Eye |
| Group A<br>Balanced Salt Solution | 3 | None | 30μl of B.S.S. | Hazy Vitreous Large fibrous Clot | Hazy Vitreous Large fibrous Clot |
| Group B<br>25 I.U. of Hyaluronidase (ACS) | 3 | None | Hyaluronidase (ACS) 25 I.U. IN 30μL | Hazy Vitreous Large fibrous Clot | Clear vitreous Retina Normal with Indirect Ophthalmoscope |
| Group C<br>50 I.U. of Hyaluronidase (ACS) | 3 | None | Hyaluronidase (ACS) 50 I.U. IN 30μL | Hazy Vitreous Large fibrous Clot | Clear vitreous Retina with Indirect Ophthalmoscope |
| Group D<br>75 I.U. of Hyaluronidase (ACS) | 3 | None | Hyaluronidase (ACS) 75 I.U. IN 30μL | Hazy Vitreous Large fibrous Clot | Clear vitreous Retina Normal with Indirect Ophthalmoscope |

FIG. 6

Hemorrhage Clearing Efficacy of Single Intravitreal Injection of
Hyaluronidase (ACS) in Human Patients with Diabetic Retinopathy

| Patient | Vitreous Hemorrhage | Dose of Hyaluronidase (ACS) Injected | Subjective Visual Activity | | Time To Hemorrhage Clearance (Days Post dose) |
|---|---|---|---|---|---|
| | | | Pre-Treatment | Post Treatment | |
| Female 54 Years Old | Left Eye of 4 Months Duration | 50 I.U. | Finger Counting at 3 Ft. Hazy Vitreous | 20/60 Clear Vitreous | 6 Days |
| Female 65 Years Old | Long Eye Duration | 50 I.U. | 20/400 Hazy Vitreous | 20/200 Clear Vitreous | 16 Days |
| Female 58 Years Old | Left Eye 1 Year Duration | 50 I.U. | Finger Counting at 5 Ft. Hazy Vitreous | 20/60 | 11 Days |
| Female 85 Years Old | Right Eye Blind Because of Optic Nerve Damage | 200 I.U. | Very Hazy Vitreous | Clear Vitreous | 8 Days |
| Female 60 Years Old | Left Eye Blind Because of Glaucoma | 70 I.U. | Very Hazy Vitreous | Clear Vitreous | 7 Days |
| Male 25 Years Old | Left Eye Penetrating Perforation Severe Intravitreal Hemorrhage | 50 I.U. | Very Hazy Vitreous Light Perception Only | Clear Vitreous Hand Movement as 1.0 Ft. | 14 Days |

USE OF HYALURONIDASE IN THE MANUFACTURE OF AN OPHTHALMIC PREPARATION FOR LIQUEFYING VITREOUS HUMOR IN THE TREATMENT OF EYE DISORDERS

This application is a continuation and claims the benefit of priority of U.S. patent application Ser. No. 09/444,003 filed Nov. 19, 1999, now U.S. Pat. No. 6,610,292, which is a continuation of and claims the benefit of priority of International Appl. No. PCT/US98/10578 filed May 22, 1998, designating the United States of America and published in English, which is a continuation-in-part and claims the benefit of priority of U.S. patent application Ser. No. 08/862,620 filed May 22, 1997, now abandoned, which is a continuation-in-part and claims the benefit of priority of U.S. patent application Ser. No. 08/561,636 filed Nov. 22, 1995, now U.S. Pat. No. 5,866,120, all of which are hereby expressly incorporated by reference in their entireties.

FIELD OF THE INVENTION

The present invention relates generally to enzyme preparations for therapeutic administration to the eyes of humans or other mammals, and more particularly to a method for utilizing one or more enzymes to treat disorders of the eye affecting the retina and/or the vitreous body of the mammalian eye.

BACKGROUND OF THE INVENTION

Anatomy of the Human Eye

In human beings, the anatomy of the eye includes a "vitreous body" which occupies approximately tour fifths of the cavity of the eyeball, behind the lens. The vitreous body is formed of gelatinous material, known as the vitreous humor. Typically, the vitreous humor of a normal human eye contains approximately 99% water along with 1% macromolecules including: collagen, hyaluronic acid, soluble glycoproteins, sugars and other low molecular weight metabolites.

The retina is essentially a layer of nervous tissue formed on the inner posterior surface of the eyeball. The retina is surrounded by a layer of cells known as the choroid layer. The retina may be divided into an optic portion which participates in the visual mechanism, and a non-optic portion which does not participate in the visual mechanism. The optic portion of the retina contains the rods and cones, which are effectual organs of vision. A number of arteries and veins enter the retina at its center, and splay outwardly to provide blood circulation to the retina.

The posterior portion of the vitreous body is in direct contact with the retina. Networks of fibrillar strands extend from the retina and permeate or insert into the vitreous body so as to attach the vitreous body to the retina.

The Causes, Treatments and Clinical Sequelae of Vitreous Hemorrhage

Diabetic retinopathy, trauma and other ophthalmological disorders sometimes result in rupture or leakage of retinal blood vessels with resultant bleeding into the vitreous humor of the eye (i.e., "vitreous hemorrhage"). Such vitreous hemorrhage typically manifests as clouding or opacification of the vitreous humor.

Vitreous hemorrhage is sometimes, but not always, accompanied by tearing or detachment of the retina. In cases where the vitreous hemorrhage is accompanied by a retinal tear or detachment, it is important that such retinal tear or detachment be promptly diagnosed and surgically repaired. Failure to promptly diagnose and repair the retinal tear or detachment may allow photoreceptor cells of the retina, in the region of the tear or detachment, to become necrotic. Such necrosis of the photoreceptor cells of the retina may result in loss of vision. Furthermore, allowing the retinal detachment to remain unrepaired for such extended period of time may result in further vitreous hemorrhage and/or the formation of fibrous tissue at the site of the hemorrhage. Such formation of fibrous tissue may result in the formation of an undesirable permanent fibrous attachment between the vitreous body and the retina.

The typical surgical procedure used for repair of retinal tears or detachment requires that the surgeon be able to look through the vitreous humor, to visualize the damaged region of the retina (i.e., "transvitreous viewing of the retina"). When vitreous hemorrhage has occurred, the presence of the hemorrhagic blood within the vitreous can cause the vitreous to become so cloudy that the surgeon is prevented from visualizing the retina through the vitreous. Such hemorrhagic clouding of the vitreous can take 6–12 months or longer to clear sufficiently to permit trans-vitreal viewing of the retina. However, in view of the potential complications which may result from delayed diagnosis or treatment of a retinal tear or detachment, it is generally not desirable to wait for such natural clearance of the hemorrhagic blood to occur.

Furthermore, even when the vitreous hemorrhage is not accompanied by retinal tear or detachment, it is often difficult to verify that retinal tear or detachment has not occurred, because the clouded vitreous prevents the physician from performing routine funduscopic examination of the retina. Moreover, the presence of hemorrhagic blood within the vitreous may significantly impair or completely obscure the patient's vision through the affected eye, and will continue to do so until such time as the hemorrhagic blood has been substantially or fully cleared.

Thus, the presence of hemorrhagic blood within the vitreous body causes multiple clinical problems including a) inability to visually examine and diagnose the site and cause of the hemorrhage and/or any accompanying tear or detachment of the retina, b) full or partial impairment of vision in the affected eye, and c) impairment or prevention of the performance of trans-vitreal surgical procedures of the type of treatment typically utilized to repair the site of hemorrhage and/or to repair any accompanying retinal tear or detachment.

In cases where vitreous hemorrhage has resulted in substantial clouding or opacification of the vitreous, the treating physician may have the option to perform a procedure known as a vitrectomy, wherein all (or a portion of) the vitreous body is removed from the interior of the eye, and replaced with a clear liquid. The performance of this vitrectomy procedure is intended to allow the surgeon to perform the necessary retinal examination and/or surgical repair of the hemorrhage and any accompanying retinal tear or detachment. Such vitrectomy procedures are highly skill intensive, and are associated with several significant drawbacks, risks and complications. Among these drawbacks, risks and complications are the potential that the act of removing the vitreous will cause further detachment or tearing of the retina and/or that such removal of the vitreous will cause further hemorrhage from the already weakened retinal blood vessels.

Prior Ophthalmic Applications of Hyaluronidase and Other Enzymes

In an effort to minimize the potential for causing further detachment or tearing of the retina during performance of the vitrectomy, it has previously been proposed in U.S. Pat. No. 5,292,509 (Hageman), to inject certain protease-free glycosaminoglycanase enzymes into the vitreous body, to cause the vitreous body to become uncoupled or "disinserted" from the retina, prior to removal of the vitreous body. Such disinsertion or uncoupling of the vitreous body is purported to minimize the likelihood that further tearing or detachment of the retina will occur as the vitreous body is removed. Examples of specific protease-free glycosaminoglycanase enzymes which may be used to bring about this vitreal disinsertion purportedly include: chondroitinase ABC, chondroitinase AC, chondroitinase B, chondroitin 4-sulfatase, chondroitin 6-sulfatase, hyaluronidase and B-glucuronidase.

Although hyaluronidase enzyme has been known to be usable for various ophthalmic applications, including the vitrectomy adjunct application described in U.S. Pat. No. 5,292,509 (Hageman), previously published studies have indicated that hyaluronidase is toxic to the retina and/or other anatomical structures of the eye when administered intravitreally at doses in excess of 1 IU, that is, at 15, 30, 50 and 150 IU of hyaluronidase. See, *The Safety of Intravitreal Hyaluronidase*; Gottlieb, J. L.; Antoszyk, A. N., Hatchell, D. L. and Soloupis, P., Invest Ophthalmol Vis Sci 31:11, 2345–52 (1990).

The ophthalmic toxicity of some hyaluronidase preparations has been confirmed by other investigators, who have proposed that such hyaluronidase preparations be used as a toxic irritant for causing experimentally-induced neovascularization of the eye, in animal toxicity models. See, *An Experimental Model of Preretinal Neovascularization in the Rabbit*; Antoszyk, A. N., Gottlieb, J. L., Casey, R. C., Hatchell, D. L. and Machemer, R., Invest Ophthalmol Vis Sci 32:1, 46–51 (1991).

Unfortunately, it has not been previously known whether the reported therapeutic activities and toxicities of hyaluronidase are universally applicable to all hyaluronidase preparations, or whether such efficacies and/or toxicities are applicable only to hyaluronidase preparations containing certain excipient materials or to hyaluronidase enzymes derived from specific sources. This is an important consideration in view of the fact that the purity and characterization (e.g., molecular weight distribution) of the various hyaluronidase preparations used in the prior art may vary, depending on the source of the hyaluronidase and the solvents and/or other formulation components with which the hyaluronidase is combined.

Purity and Characterization of Hyaluronidase Preparations Previously Used for Ophthalmic Administration The term "hyaluronidase" is commonly used to describe a group of endo-B-glucuronidase enzymes which depolymerize certain mucopolysaccharides, such as hyaluronic acid. Myer, K. et al., *The Enzymes*; Vol. 4, 2d, Ed., pp 447, Academic Press, Inc., New York (1960).

Hyaluronidase causes hydrolysis of the endo-N-acetyl hexosaminic bonds of hyaluronic acid and of the chondroitin sulfate acids A and C, primarily to tetrasaccharide residues.

Significant evidence indicates that hyaluronidase enzymes derived from different sources differ in enzyme molecular weight distribution and in specific enzymatic activities. Such variability in molecular weight distribution and specific enzymatic activity are noteworthy considerations in view of the fact that hyaluronidase enzymes may be isolated from a variety of sources, including bovine testes, ovine testes, certain bacteria such as streptomyces and certain invertebrate animals such as leeches.

The Wydase® hyaluronidase preparation is reported to have been previously administered to the eyes of mammals for various clinical and experimental applications, including the treatment of glaucoma and the promotion of liquefaction of the vitreous body during vitrectomy procedures wherein the vitreous body is removed from the eye.

Although some hyaluronidase preparations have been reported to exhibit desirable therapeutic effects when injected into or administered topically to the eye, the potential toxicities of hyaluronidase and/or the thimerosal preservative are cause for concern regarding the safety of routine clinical administration of such preparations by intraocular injection.

Accordingly, there exists a need in the art for the formulation and development of a new hyaluronidase preparation which may be administered to the eye at dosage levels which are sufficient to bring about optimal therapeutic effects, but which do not cause ocular toxicity.

Additionally, in view of the above-discussed problems associated with the slowness of natural clearance of hemorrhagic blood from the vitreous body, there exists a need in the art for the elucidation and development of new methods and procedures for accelerating the clearance of hemorrhagic blood from the vitreous body of the eye so as to permit trans-vitreal viewing of the posterior aspect of the eye, including the retina, without the need for removal of the vitreous body (i.e., total or partial vitrectomy).

Additionally, there is a need for the prevention and treatment of various disorders of the mammalian eye which result from damage or pathology to the vascularization of the retina or which result in damage to the blood-retinal barrier.

SUMMARY OF THE INVENTION

An enzymatic method is provided for treating ophthalmic disorders of the mammalian eye. Prevention of neovascularization and the increased rate of clearance from the vitreous of materials toxic to retina is accomplished by administering an amount of hyaluronidase effective to liquefy the vitreous humor of the treated eye without causing toxic damage to the eye. Liquefaction of the vitreous humor increases the rate of liquid exchange from the vitreal chamber. This increase in exchange removes those materials and conditions whose presence causes ophthamological and retinal damage.

A method for inducing liquefaction of a vitreous humor to prevent a disorder of a mammalian eye, comprising the step of contacting with the vitreous humor of a mammalian eye an amount of hyaluronidase effective to liquefy the vitreous humor, whereby the disorder is prevented without causing toxic damage to the mammalian eye.

Preferably, the method is carried out for the purpose of treating proliferative diabetic retinopathy, age-related macular degeneration, amblyopia edema. The hyaluronidase enzyme may be in a liquid solution, and the step of contacting of the enzyme with the vitreous humor comprises, injecting said liquid solution into the vitreous humor. The hyaluronidase is contacted with the vitreous in the absence of thimerosal.

In one embodiment, the hyaluronidase is contacted with the vitreous humor at a dose of 5–200 International Units. In another embodiment the hyaluronidase is contacted with the vitreous humor at a dose of 1 International Units. The hyaluronidase may be administered in multiple doses, and a single intravitreal injection may have an injectate volume of less than 100:1.

In another embodiment, the hyaluronidase is devoid of hyaluronic acid lysing activity having a molecular weight above approximately 100,000 when determined by 10% SOS PAGE electrophoresis. Also, the hyaluronidase is devoid of gelatinolytic activity having a molecular weight between approximately 60,000–100,000 when determined by 10% SOS PAGE electrophoresis. Further, the hyaluronidase enzyme is devoid of caseinolytic activity having a molecular weight above approximately 45,000 when determined by 10% SDS PAGE electrophoresis. Moreover, the hyaluronidase is devoid of hyaluronidase matter having a molecular weight above approximately 100,000 when determined by 4–20% SOS PAGE electrophoresis. Additionally, the hyaluronidase is devoid of hyaluronidase matter having a molecular weight between approximately 50,000–60,000 when determined by 4–20% SOS PAGE electrophoresis. Furthermore, the hyaluronidase is devoid of hyaluronidase matter having a molecular weight below approximately 20,000 when determined by 4–20% SOS PAGE electrophoresis.

In another embodiment, the hyaluronidase is prepared in a solution for injection which is free of thimerosal and which has a formulation comprising hyaluronidase up to 8000 IU, the lactose is at 5.0–130.0 mg, and the phosphate at 0.01–100.0 mmoles. In yet another embodiment, the hyaluronidase is prepared in a solution for injection which is free of thimerosal and which has a formulation comprising hyaluronidase at 6500 IU, lactose at 5.0 mg, and phosphate at 0.02 mmoles. In still another embodiment, the hyaluronidase is prepared in a solution for injection which is free of thimerosal and which has a formulation such that the hyaluronidase is at 500–1000 IU, the lactose is at 5.0–10.0 mg, and the phosphate is at 0.01–10.0 mmoles.

In another embodiment of the present invention, a method for treating a disorder of a mammalian eye comprises the step of contacting with a vitreous humor of said mammalian eye an amount of hyaluronidase effective to treat said disorder without causing toxic damage to said mammalian eye. Here, the vitreous humor is free of hemorrhagic blood that permits viewing of a retina of said mammalian eye. Moreover, the contacting step is practiced in the absence of vitrectomy.

BRIEF DESCRIPTION OF THE DRAWINGS

FIG. 2 is a table which summarizes the zymographically determined hyaluronic acid lysing, gelatinolytic and caseinolytic activities of the hyaluronidase ACS of the present invention, in comparison to bovine hyaluronidases of types VI-S, IV-S and I-S and ovine hyaluronidase of type V.

FIG. 3 is a table which summarizes the toxic effects of single dose intravitreal injections of BSS, BSS+ thimerosal, hyaluronidase ACS and hyaluronidase Wydase® in rabbits, in accordance with Example 1 herebelow.

FIG. 4 is a table which summarizes the efficacy of single-dose intravitreal hyaluronidase ACS in rabbits, in accordance with Example 2 herebelow.

FIG. 5 is a table which summarizes the safety and efficacy of multiple doses of intravitreal hyaluronidase ACS in rabbits, in accordance with Example 2 herebelow.

FIG. 6 is a table which summaries the hemorrhage-clearing efficacy of single-dose hyaluronidase ACS in human patients having diabetic retinopathy, in accordance with Example 9 herebelow.

DETAILED DESCRIPTION OF THE INVENTION

Figure 1:
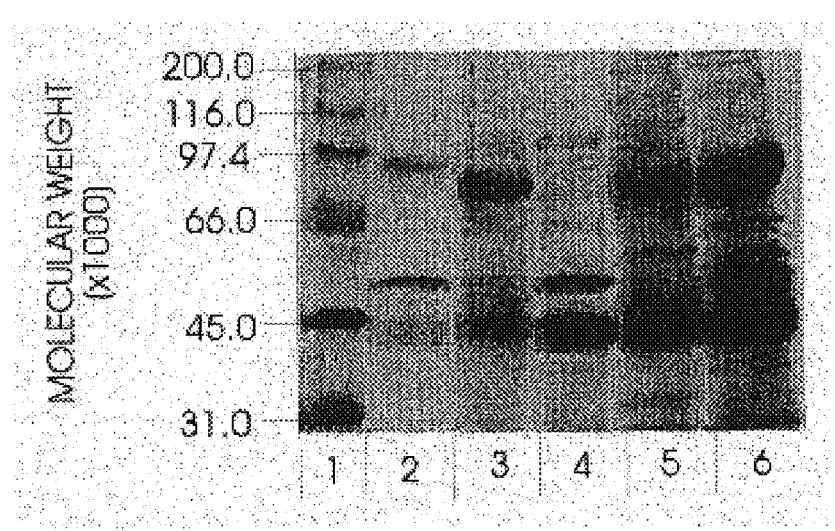
FIG. 1 shows an electrophoresis gel having lanes 1–6, said lanes indicating 1) molecular weight standards from 31,000 through 200,000, 2) ovine hyaluronidase ACS, 3) bovine hyaluronidase type VI-S, 4) ovine hyaluronidase type V, 5) bovine hyaluronidase type IV-S and 6) bovine hyaluronidase type I-S.

The following detailed description and the accompanying examples are provided for purposes of describing and explaining certain preferred embodiments of the invention only, and are not intended to limit the scope of the invention in any way.

Enzymatic Method for Accelerating Clearance of Hemorrhagic Blood from the Vitreous of the Eye In accordance with the invention, applicant has determined that certain types of enzymes, when contacted with the vitreous humor following hemorrhage thereinto, will accelerate the rate at which the hemorrhagic blood is cleared from the vitreous humor.

In this regard, Applicant has devised a method for accelerating clearance of hemorrhagic blood from the vitreous of the eye, said method generally comprising the step of contacting, with the vitreous humor, a quantity of hyaluronidase at a dose which is sufficient to accelerate the clearance of hemorrhagic blood from the vitreous without causing damage to the retina or other tissues of the eye. Preferably, the hyaluronidase is selected to have a molecular weight distribution which allows the hyaluronidase to be administered intravitreally at doses above 1 IU, and preferably above 15 IU, and advantageously above 75 IU, in the absence of thimerosal, without causing toxic damage to the retina or other tissues of the eye. This hemorrhage-clearing method of the present invention may be performed without any vitrectomy or other surgical manipulation or removal of the vitreous humor, thereby avoiding the potential risks and complications associated with such vitrectomy procedures.

The preferred route of administration of these hemorrhage-clearing enzymes is by intraocular injection directly into the vitreous body. Alternatively, however, the hemorrhage-clearing enzyme(s), of the present invention may be administered by any other suitable route of administration (e.g., topically) which results in sufficient distribution of the enzyme(s) to the vitreous body to cause the desired hemorrhage-clearing effect.

The preferred injectable solution may contain, a hyaluronidase which has a molecular weight distribution which allows it to be administered intravitreally at doses above 1 IU, and preferably above 15 IU, and advantageously above 75 IU, without causing toxic damage to the eye, along with inactive ingredients which cause the solution to be substantially isotonic, and of a pH which is suitable for injection into the eye. This preferred hyaluronidase preparation is preferably devoid of thimerosal. Such solution for injection may be initially lyophilized to a dry state and, thereafter, may be reconstituted prior to use.

A Preferred Hyaluronidase Preparation for Ophthalmic Administration

A general formulation for an injectable thimerosal-free, hyaluronidase preparation, of the present invention is shown in Table 1 as follows:

TABLE 1

General Formulation

| Ingredient | Quantity |
| --- | --- |
| Hyaluronidase ACS | up to 8000 International units |
| Lactose USP | 5.0 mg–130.0 mg |
| Phosphate USP | 0.01–100 mmoles |

These formulation ingredients are initially dissolved in sterile water, sterile filtered and subsequently lyophilized to a dry composition. The lyophilized composition is packaged for subsequent reconstitution prior to use, in a suitable solvent such as sterile isotonic saline solution or balanced salt solution. Such balanced salt solution typically contains: 0.64% sodium chloride, 0.075% potassium chloride, 0.048% calcium chloride dehydrate, 0.03% magnesium chloride hexahydrate, 0.39% sodium acetate trihydrate, 0.17% sodium citrate dihydrate, sodium hydride/hydrochloric acid to adjust the pH, and as much water (q.s.) as necessary to bring the solution to the final volume for injection.

The term "hyaluronidase ACS" as used herein describes a preferred hyaluronidase solution for intravitreal injection which is devoid of thimerosal and which is devoid of hyaluronidase molecular weight fractions above 100,000, between 50,000–60,000 and below 20,000. One such hyaluronidase is available commercially from Calbiochem Biochemicals, P.O. Box 12087, La Jolla, Calif. 92039–2087 (manufactured by Biozyme, San Diego, Calif.). Applicants have determined that this specific molecular weight distribution of the hyaluronidase ACS results in less ophthalmic toxicity than other hyaluronidase preparations, while exhibiting desirable therapeutic efficacy in a number of ophthalmic applications.

FIG. 1 shows an electrophoresis gel (4–20% Gradient SDS-PAGE) which demonstrates the molecular weight distribution of the preferred hyaluronidase ACS in comparison to the molecular weight distributions of bovine type VI-S, IV-S and I-S and ovine type V hyaluronidases obtained from SIGMA Chemical Company, P.O. Box 14508, St. Louis, Mo. 63178. Standardized amounts (i.e., equivalent units of hyaluronidase activity) of each enzyme was loaded into each lane (lanes 2–6) of the electrophoresis gel shown in FIG. 1. Lane 1 of the electrophoresis gel shown in FIG. 1 contains molecular weight markers at 200,000, 116,000, 97,400, 66,000, 45,000, and 31,000, respectively. Lanes 2–6 of the electrophoresis gel shown in FIG. 1 contain the respective hyaluronidase preparations tested, as follows:

| LANE | WHAT IS IN THE LANE |
| --- | --- |
| 2 | Hyaluronidase ACS |
| 3 | Bovine Hyaluronidase type VI-S |
| 4 | Ovine Hyaluronidase type V |
| 5 | Bovine Hyaluronidase type IV-S |
| 6 | Bovine Hyaluronidase type I-S |

Lane 2 shows that the molecular weight distribution of the hyaluronidase ACS includes molecular weight fractions of 97,400, 50,000 (approx.) and 45,000 (approx.), but is clearly devoid of molecular weight fractions above 100,000, between 50,000–60,000 and below 20,000.

Lanes 3, 4, 5 and 6 of the electrophoresis gel of FIG. 1 show that all of the bovine testicular hyaluronidases of types VI-S, IV-S and I-S and ovine testicular hyaluronidase of type V tested differ from the hyaluronidase ACS of the present invention in that they include molecular weight fractions between 50,000–60,000 and below 20,000. Also, three (3) of the four (4) testicular hyaluronidase tested (i.e., types VI-S, IV-S and I-S) included hyaluronidase molecular weight fractions which were in excess of 100,000.

Additionally, zymograms were performed to compare the relative lytic activities of standardized amounts (i.e., equivalent units of hyaluronidase activity) of the above-described hyaluronidase ACS, type VI-S, V, IV-S and I-S hyaluronidase upon hyaluronic acid, gelatin and casein. With respect to FIG. 2, the specific methods by which each of these zymograms was performed are as follows:

Zymogram for Gelantinolytic Activity

GELATIN-1 mg/ml gelatin; 10% polyacrylamide; overnight buffer=50 mM Tris HCl, 5 mM $CaCl_2$, 0.05% Triton X-100 pH 7.5; stain Coomassie blue; destain 10% acetic acid/50% methanol.

Zymogram for Caseinolytic Activity

CASEIN-4 mg/ml; 15% polyacrylamide; overnight buffer=50 mM Tris HCl, 5 mM $CaCl_2$, 0.05% Triton X-100 pH 7.5; stain Coomassie blue; destain 10% acetic acid/50% methanol.

Zymogram for Hyaluronic Acid Lysing Activity

HYALURONIC ACID-2 mg/ml; 10% polyacrylamide; overnight buffer=phosphate buffered saline, pH 7.4; stain 0.5% alcian blue in 3% acetic acid; destain 10% acetic acid/50% methanol.

The results of these hyaluronic acid, gelatin and casein zymograms are summarized in the table of FIG. 2. Notably, the preferred hyaluronidase ACS of the present invention is devoid of hyaluronic acid lysing molecular weight fractions above approximately 100,000 when determined by 10% SDS PAGE electrophoresis while each of the testicular hyaluronidases tested (i.e., types VI-S, V, IV-S and I-S) contained hyaluronic acid lysing molecular weight fractions above 100,000.

Similarly, the hyaluronidase ACS of the present invention was devoid of gelatinolytic molecular weight fractions between approximately 60,000–100,000, while each of the testicular hyaluronidases tested included gelatinolytic molecular weight fractions between approximately 60,000–100,000 000 when determined by 10% SDS PAGE electrophoresis.

Also, the hyaluronidase ACS of the present invention was devoid of caseinolytic molecular weight fractions above approximately 45,000 while each of the testicular hyaluronidases (i.e., types VI-S, V, IV-S and I-S) tested did contain caseinolytic molecular weight fractions above approximately 45,000 when determined by 10% SDS PAGE electrophoresis.

The specific molecular weight distribution and specific enzyme activity profile of the preferred hyaluronidase ACS of the present invention, and/or the exclusion of thimerosal from its formulation, provides a hyaluronidase preparation which is non-toxic to the eye when administered at dosage levels at which other hyaluronidase preparations would cause toxic effects.

For use in the examples set forth herebelow, the preferred hyaluronidase ACS is prepared in a thimerosal free formulation by the method and general formula described herebelow and shown in Table 1. More specifically, the hyalu ronidase ACS used in the following examples is prepared in accordance with the specific formulation shown in Table 2 herebelow:

TABLE 2

Specific Formulation A

| Ingredient | Quantity |
|---|---|
| Hyaluronidase ACS | 7,200 IU |
| Lactose USP | 5.0 mg |
| Phosphate USP | 0.02 mmoles |

Alternatively, another specific formulation useable for unit-dose applications is shown in Table 3 as follows:

TABLE 3

Specific Formulation B

| Ingrediant | Quantity |
|---|---|
| Hyaluronidase ACS | 500–1000 IU |
| Lactose USP | 5.0–10.0 mg |
| Phosphate USP | 0.1–10.0 mmoles |

In still another alternative specific formulation, the hyaluronidase ACS is supplied in a lyophilized form and the components are shown in Table 4 as follows:

TABLE 4

Specific Formulation C

| Ingredient | Quantity |
|---|---|
| Hyaluronidase ACS | 450 IU |
| Lactose USP | 10.0 mg |
| Potassium Phosphate Monobasic USP | 0.098 mg |
| Potassium Phosphate Dibasic USP | 10.0 mg |
| Diluent Amount (0.9% NaCl) | 0.3 ml or 0.18 ml |
| Injection Volume | 0.5 ml or 0.03 ml |

Diluent amounts and injection volumes are listed above for a 75 IU dose. Diluent amounts may be changed to vary dosage.

In still another alternative, specific formulation, the hyaluronidase ACS is supplied in a liquid form and is shown in Table 5 as follows:

TABLE 5

Specific Formulation C

| Ingredient | Quantity |
|---|---|
| Hyaluronidase ACS | 1,500 IU |
| Lactose USP | 1.25 mg |
| Potassium Phosphate Monobasic USP | 0.305 mg |
| Potassium Phosphate Dibasic USP | 0.48 mg |
| Injection Volume | 0.05 ml |
| Dose | 75 IU |

It is contemplated that all ingredients may be reduced proportionally to achieve lower dosages with the same injection volume. Also, the quantity of lactose may be reduced by one-half or one-quarter.

TABLE 6

Specific Formulation D

| Ingredient | Quantity |
|---|---|
| Hyaluronidase ACS | 6,500 IU |
| Lactose USP | 5.0 mg |
| Phosphate USP | 0.02 mmoles |

As described in the following examples, the specific formulation A of the hyaluronidase ACS set forth in Table 2 (above) may be injected directly into the posterior chamber of the eye at dosage levels which bring about desirable therapeutic affects, including but not necessarily limited to the vitreous hemorrhage clearing effect of the present invention, without causing significant toxicity to the eye or associated anatomical structures. Alternatively, the specific formulations B or C of hyaluronidase ACS may be so injected. Still another alternative provides for the use of specific formulation D of hyaluronidase ACS set forth in Table 6 in the methods of the present invention.

Ophthalmic Toxicities of Thimerosal, Hyaluronidase ACS and Hyaluronidase (Wydase®) in Rabbits

EXAMPLE 1

Fifty-two (52) healthy rabbits of the New Zealand Cross Variety (26 male, 26 female) weighing 1.5 kg to 2.5 kg, were individually marked for identification and were housed individually in suspended cages. The animals received a commercially available pelleted rabbit feed on a daily basis, with tap water available ad libitum.

The animals were divided into thirteen groups of 4 animals each (2 male, 2 female). Two animals in each group (1 male, 1 female) were selected for pretreatment fundus photography and fluorescein angiography.

The fundus photography was performed by restraining the animals and visualizing the optic nerve, retinal arcades with fundus with a KOWA® RC-3 Fundus Camera loaded with Kodak Gold 200 ASA film.

The fluorescein angiography involved a 1.5 ml injection of 2% sterile fluorescein solution via the marginal ear vein. Approximately 30 seconds post-injection the fluorescein was visualized upon localization of the optic nerve, retinal vessels and fundus.

The following day, each animal was anesthetized by intravenous administration of a combination of 34 mg/kg of ketamine hydrochloride and 5 mg/kg xylazine. The eyelids were retracted using a lid speculum, and the eyes were disinfected with an iodine-providone wash.

Experimental treatments of either balanced salt solution (BSS), BSS+thimerosal, hyaluronidase (Wydase®) or hyaluronidase ACS were administered by injection using a 1 cc tuberculin syringe with a 30 gauge, 0.5 inch needle attached thereto. The hyaluronidase ACS solution utilized in this example was free of thimerosal and constituted the specific hyaluronidase ACS formulation set forth in Table 2 hereabove.

The experimental treatments administered to each animal group were as follows:

| Group # | Treatment |
|---|---|
| 1 | BSS |
| 2 | BSS + 0.0075 mg Thimerosal |
| 3 | BSS + 0.025 mg Thimerosal |
| 4 | Hyaluronidase (Wydase) 1 IU |
| 5 | Hyaluronidase (Wydase) 15 IU |
| 6 | Hyaluronidase (Wydase) 30 IU |
| 7 | Hyalurunidase (Wydase) 50 IU |
| 8 | Hyaluranidase (Wydase) 150 IU |
| 9 | Hyaluronidase ACS 1 IU |
| 10 | Hyaluronidase ACS 15 IU |
| 11 | Hyaluronidase ACS 30 IU |
| 12 | Hyaluronidase ACS 50 IU |
| 13 | Hyaluronidase ACS 150 IU |

The day following the injections (Day 1), the 26 animals which were subjected to the fundus photography and fluorescein angiography were observed using the same methods as for the pre-dose examination.

On Day 2 following the injections, the 13 male rabbits that had received the fundus photography and fluorescein angiography at pre-dose and Day 1, as well as the 13 female rabbits that were not selected for photography were euthanized with a sodium pentobarbital based drug. The eyes were then surgically removed and placed in a fixture solution of 2.5% glutaraldehyde with 0.1 M phosphate buffered saline at pH 7.37.

Alternatively, one randomly selected rabbit was euthanized by pentobarbital injection but then fixed by intracardiac injection of the glutaraldehyde solution into the left ventricle to determine the effect of the fixation procedure on the histology findings within the enucleated eyes.

On Day 7, the 13 female rabbits that had been previously photographed and angiography performed were subjected to the same observations following the methods previously described.

The remaining 26 animals were euthanized as described above 7 days after dosing. The eyes were fixed in the same manner as those which had been fixed on day 2. Also, one randomly selected rabbit was subjected to the same intracardiac glutaraldehyde fixation procedure described hereabove for the previously randomly selected animal.

The eyes of the animals treated in this example were examined grossly and microscopically for evidence of treatment-related toxicities. A table setting forth a summary of the histological evidence of toxicity or non-toxicity in each treatment group, is set forth in FIG. 3.

In summary, the eyes of the BSS-treated control group were free of toxicity at 2 and 7 days post-dose.

The eyes of the Group No. 2 animals treated with BSS+ thimerosal (0.0075 mg) were free of toxicity at day 2, but exhibited evidence that there was a breakdown of the blood-retinal barrier at day 7.

The Group No. 3 animals treated with BSS+thimerosal (0.025 mg) exhibited severe treatment-related toxic effects, at days 2 and 7 post-dose.

The Group No. 4 animals treated with Wydase® at the 1 IU dose were free of toxicity at days 2 and 7, however, the eyes of the animals in Group Nos. 5–8 treated with Wydase® at dosages ranging from 15 IU-150 IU exhibited generally dose-related toxic effects at days 2 and 7 post-dose.

The eyes of animals in treatment Groups Nos. 9–13 treated with hyaluronidase ACS, at dosages ranging from 1 IU through 150 IU, were generally free of evidence of toxic effects at days 2 and 7 post-dose. Nevertheless, there was some fluorescein leakage observed in animals treated with the 150 IU doses.

Accordingly, it is concluded that thimerosal and the thimerosal-containing Wydase® formulation do cause toxic effects in the eyes of rabbits at the dosages tested, however, hyaluronidase ACS caused no toxic effects in these animals at the dosages tested.

The results of the examinations conducted on day 7 are summarized in FIG. 3. As shown, FIG. 3, significant toxic effects were observed on day 7 in the eyes of rabbits treated with BSS plus thimerosal (0.0075 mg) and hyaluronidase (Wydase) at all doses between 1 IU–150 IU. In contrast, no toxic effects were observed in the eyes of animals treated with hyaluronidase ACS at doses from 1–150 IU.

Safety and Efficacy of Hyaluronidase ACS Injected Intravitreally in Rabbit Eyes

EXAMPLE 2

In this example, 12 healthy rabbits of the New Zealand Cross variety were marked for identification and individually housed in suspended cages. The animals received commercially pelleted rabbit feed on a daily basis and tap water was available ad libitum.

The animals were randomly divided into four (4) treatment groups of three (3) animals each.

Initially, the eyes of each animal were examined by dilation with 1–2 drops of 10% tropicamide followed by gross examination, indirect ophthalmoscopy using a 20 diopter lens, and slit lamp examination of the anterior anatomy of the eye.

Following the initial examination of the animals eyes, 100:1 or 10:1 of blood was injected intravitreally into each eye of each animal.

On day 2, the animals of each treatment group received a single intravitreal injection of either BSS or hyaluronidase ACS into the right eye, in accordance with the following treatment schedule:

| Group # | Left Eye | Treatment Right Eye |
|---|---|---|
| A | None | BSS(30:1) × 1 |
| B | None | 25 IU Hyaluronidase ACS in 30:1 × 1 |
| C | None | 50 IU Hyaluronidase ACS in 30:1 × 1 |
| D | None | 75 IU Hyaluronidase ACS in 30:1 × 1 |

The hyaluronidase ACS preparation used in this experiment was the formulation described hereabove and shown in Table 2.

On days 3, 5, 7, 14 and 21 the eyes of each animal were again examined by slit-lamp to evaluate the cornea, anterior chamber and iris. In addition, the eyes of each animal were dilated with 10% tropicamide solution and the retina was examined by indirect ophthalmoscopy with a 20 diopter lens.

The observed hemorrhage-clearing efficacy of hyaluronidase ACS is summarized in FIG. 4. In general, the left eye (untreated) of each animal in each treatment group contained a hazy vitreous and some blood clots, due to the quantity of blood which had been injected therein. The right eyes of the BSS treated (control) animals of Group A also contained hazy vitreous and some blood clots, while the right eyes of all hyaluronidase-treated animals in Treatment Groups B–D contained vitreous which was clear and through which trans-vitreal visualization of the retina was possible. Furthermore, the retinas of the rights eyes of all animals in Treatment Groups B–D appeared normal and free of treatment-related toxicity.

The results of this experiment indicate that intravitreally administered hyaluronidase ACS was effective at single doses of 25, 50, and 75 IU, to accelerate the rate at which blood was cleared from the eyes of the treated animals and further that such single doses of hyaluronidase ACS administered in this experiment did not cause observable toxic effects in the eyes of the rabbits treated in this experiment.

In a variation, the example was performed exactly as above except that instead of administration of a single dose, multiple doses were administered in the amount of four (4) consecutive doses of hyaluronidase ACS at 2 week intervals. The observations following each dose were consistent and are summarized in FIG. 5. In general, the left eye (untreated) of each animal in each treatment group, contained hazy vitreous humor and some blood clots, due to the quantity of blood which had been injected therein. The right eyes of the BSS treated (control) animals of Group A also contained hazy vitreous and some blood clots, while the right eyes of all animals in treatment Groups B–D (i.e., the animals treated with hyaluronidase ACS) contained clear vitreous through which trans-vitreal visualization of the retina was possible. Furthermore, the retinas of the right eyes of all animals in treatment Groups B–D appeared to be normal and free of treatment-related toxicity, even after multiple doses of the hyaluronidase ACS.

The results of this experiment indicate that intravitreally administered hyaluronidase ACS was effective, at single doses of 25, 50, and 75 IU×4, to accelerate the rate at which blood was cleared from the eyes of rabbits and further that such doses of hyaluronidase ACS did not cause observable toxic effects in the eyes of the treated rabbits, even after four (4) consecutive doses of hyaluronidase ACS administered at 2 week intervals.

Safety and Efficacy of Hyaluronidase ACS Injected Intravitreally in Human Eyes

EXAMPLE 3

The primary objective of this study was to determine if a balanced salt solution containing a highly purified hyaluronidase extract from ovine testicular tissue could be injected into the vitreous of visually impaired eyes without eliciting any serious ocular adverse effects.

Materials and Methods

Balanced Salt Solution (BSS) was employed as the placebo control, and was obtained from Allergan Pharmaceuticals (Irvine, Calif.). The BSS contained 0.64% sodium chloride, 0.075% potassium chloride, 0.048% calcium chloride dihydrate, 0.03% magnesium chloride hexahydrate, 0.39% sodium acetate trihydrate, 0.17% sodium citrate dihydrate, sufficient sodium hydroxide/hydrochloric acid for adjustment of pH to 7.1–7.2, and water for injection (qs. 100%). Thirty microliter aliquots of BSS or hyaluronidase specific formulation D (Table 6) were loaded into a 300 µl microsyringe fitted with a 29 gauge needle 0.5 inches in length. The loaded microsyringe were then used to inject the material into the vitreous of the patient's eye.

Initially, eight human subjects with at least one visually impaired eye were randomly assigned to receive intravitreally either 50 µl of 50 IU of hyaluronidase ACS in BSS or BSS alone (3:1 ratio). After one month of follow-up to assure the 50 IU dosage was well-tolerated, a second group of six visually impaired subjects were enrolled in the study and randomly assigned to a higher hyaluronidase ACS dosage group (100 IU) or the BSS control in a 2:1 ratio.

Procedures used to evaluate the safety of the test articles were completed at various intervals throughout the study, and included indirect ophthalmoscopy, fundus photography, fluorescein angiography, electroretinography, external eye examination, slit lamp biomicroscopy, applanation tonometry, pachymetry, and autorefraction.

A concurrent placebo control group was included in the study so that adverse events peculiarly related to hyaluronidase ACS could be distinguished from those attributable to the vehicle (BSS)/injection procedure. Only visually impaired eyes were treated, moreover, since the test articles were injected proximate to the retina and any untoward responses of a serious nature could have been sight threatening. Patients were assigned to treatment using a computer generated randomization scheme beginning with the number 601 for the first phase of the study, and 701 for the second. Neither the patients nor investigators were aware of whether it was the BSS vehicle or hyaluronidase ACS/BSS solution that was being injected intravitreally.

Following establishment of a baseline for each patient, the subjects were injected with either the enzyme or the placebo control. Patients were placed in a sitting position on a comfortable chair. One or two drops of a local anesthetic were topically instilled into the eye that was to be treated, after which the patient was asked to look down and a sterile cotton swab soaked in Proparacaine Hydrochloride Ophthalmic solution was applied for 10 seconds to an area on the sclera approximately 4–5 mm above the cornea (superior position/12:00 meridian). The test article was then injected into the vitreous through a 29 gauge needle attached to a 200 µl microsyringe that was inserted up to the full length of the needle at the site of application of the second anesthetic.

Results

Although only infrequently attaining statistical significance, the slit lamp biomicroscopy data suggested that a substantially higher proportion of patients treated with the hyaluronidase ACS/BSS preparations as opposed to BSS alone exhibited anterior segment pathologic changes, the most prominent being the presence of cells and flare in the anterior chamber. After the sixth (one month posttreatment) visit, however, no intergroup differences were observed for any of the slit lamp assessed variables.

Retinal/cortical responses, as measured by electroretinography/visual evoked potential deteriorated over time in one patient treated with BSS and two who were given 50 IU of hyaluronidase ACS/BSS. However, alterations in electroretinographic patterns were always bilateral and did not occur in either the treated or untreated eyes of the patients assigned to high dose (100 IU) hyaluronidase ACS/BSS, nor did fluorescein angiographic test results indicate that retinal ischemia was present in any eye irrespective of treatment.

The indirect ophthalmoscopic exams revealed liquefaction and the establishment of posterior vitreal detachment (PVD) in the eyes of the test subjects. The vitreous was characterized as exhibiting a high degree of motility and/or liquefaction soon after injecting the test articles, which was expected for the hyaluronidase ACS-containing preparations. Certain test eyes injected the BSS control should liquefaction and PVD, which was likely present before treatment, since the latter did not possess any enzymatic activity and was given in very small volume (30 μl).

Concerning PVD, in the first group of patients, four of the six patients to be treated with hyaluronidase ACS displayed the absence of PVD by slit lamp biomicroscopy (i.e., 601, 602, 604, and 606)(See Table 6 below). After treatment, each of these subjects showed the presence of PVD. The results from the second group of patients were less clear, due to difficulties in imaging the vitreous using slit lamp microscopy.

TABLE 6

Human Safety Study with 50:1 and 100:1 Hyaluronidase ACS Injection Intravitreally

| Number | Enzyme Dose | Treated Eye | Split Lamp Diomicroscopy of Presence of PVD Baseline Treated | | Day for PYD | Vitreous Motility |
|---|---|---|---|---|---|---|
| 601 | 50 | OD | NO | YES | 2 Days | +3/+4 |
| 602 | 50 | OD | NO | YES | 1 Day | +4 |
| 603 | BSS | OD | YES | YES | — | +3 |
| 604 | 50 | OD | NO | YES | 1 Day | +3 |
| 605 | BSS | OS | YES | YES | — | +3/+4 |
| 606 | 50 | OD | NO | YES | 14 Days | +3/+4 |
| 607 | 50 | OD | YES | YES | — | +3/+4 |
| 608 | 50 | OD | YES | YES | — | +3 |
| 701 | 100 | OS | NO | ? | — | +2 |
| 702 | 100 | OD | NO | ? | | +4 |
| 703 | BSS | OD | YES | YES | — | |
| 704 | 100 | OS | NO | ? | | |
| 705 | 100 | OD | NO | Yes | 1 Day | |
| 706 | BSS | OS | NO | NO | | |

Given the results from Example 2 where injection of hyaluronidase ACS into the vitreous of rabbits at various doses up to 150 IU did not result in any significant histopathologic changes in an earlier preclinical study, it was expected that doses below 150 IU would be well-tolerated in humans. Consistent with this expectation, the intravitreal administration of hyaluronidase ACS/BSS into visually impaired eyes in the current trial elicited few symptoms, all of which were believed attributable to the injection procedure itself as they occurred with comparable frequency in each of the study groups, and treatment-related adverse sequelae were relatively mild and of short duration.

Furthermore, treatment of human eyes with hyaluronidase ACS was observed to increase the incidence of observed posterior vitreal detachment. The observed increase in PVD in patients injected intravitreally with hyaluronidase ACS shows that the methods of the present invention are effective in inducing liquefaction and detachment of the vitreal humor. Thus, the results of the present study indicate that hyaluronidase ACS can be injected into the vitreous of humans without eliciting any serious or long-term ocular complications.

Use of Hyaluronidase to Accelerate the Clearance of Hemorrhagic Blood from the Vitreous of the Eye Example 4 set forth herebelow describes cases in which intravitreal hyaluronidase ACS was used to accelerate the clearance of hemorrhagic blood from the vitreous of the eye. In Example 4, the hyaluronidase used was the thimerosal-free hyaluronidase ACS formulation described above and shown in Table 2.

EXAMPLE 4

Accelerated Hemorrhage Clearance following Intravitreal Hyaluronidase

In this experiment, six (6) human patients (5 female, 1 male) who presented with vitreous hemorrhage were treated with single intravitreal injections of hyaluronidase ACS at dosages of 50–200 IU The hyaluronidase ACS administered in this experiment was prepared by the formulation, described hereabove and shown in Table 2.

All of the patients treated in this experiment had a history of diabetic retinopathy, and were found to have vitreous hemorrhages of varying duration. In each patient, the amount of blood present in the vitreous was sufficient to prevent viewing of the retina by standard funduscopic means.

Each patient received a single intravitreal injection of hyaluronidase ACS. Four (4) patients received a dose of 50 IU, one (1) patient received a dose of 70 IU, and one (1) patient received a dose of 200 IU.

The observed results of this experiment are summarized in FIG. 6.

In the six (6) patients treated in this example, the hemorrhagic vitreous became sufficiently clear to permit transvitreal viewing of the retina within 6–16 days of the single intravitreal injection of the hyaluronidase ACS. Such clearing of the vitreous was subjectively determined to have occurred significantly faster than that which would have been expected to occur in these patients without hyaluronidase treatment.

It should be noted that unlike the fluorscein leakage observed at higher doses of hyaluronidase ACS in rabbits, no toxicity was observed in the present human based study.

The Use of Hyaluronidase to Treat Other Ophthalmological Disorders

Applicants have additionally observed the efficacy of a single intravitreal administration of hyaluronidase ACS, at an experimental dose, in treating certain ophthalmological disorders. Patients who suffered from previously diagnosed disorders of the eye, including proliferative diabetic retinopathy, age-related macular degeneration, amblyopia, retinitis pigmentosa, macular holes, macular exudates and cystoid macular edema, have exhibited improvement in the clinical symptoms of these disorders upon treatment with hyaluronidase ACS.

Applicants have also determined that the hyaluronidase ACS formulation of the present invention is capable of being administered intravitreally at doses of or in excess of 1 IU without causing toxic damage to the eye and thus is useable to effect prompt liquefaction of the vitreous body and concomitantly the disconnection or detachment of the vitreous body from the retina and other tissues (e.g., epiretinal membranes, macula). As a result of this vitreal liquefaction and detachment, the physical pulling forces of the vitreous on the retina and other tissues are minimized and the rate of natural turnover of fluids within the vitreous is accelerated. Accordingly, Applicants' hyaluronidase ACS formulation is particularly suitable for the treatment of many disorders (e.g., proliferative diabetic retinopathy, age-related macular degeneration, amblyopia, retinitis pigmentosa, macular holes, macular exudates and cystoid macular edema) which benefit from liquefaction/disconnection of the vitreous and/or accelerated clearance of toxins or other deleterious substances (e.g., angiogenic factors, edema fluids, etc.) from the posterior chamber of the eye and/or from tissues adjacent the posterior chamber (e.g., the retina or macula). Moreover, liquefaction of the vitreous is also believed to remove the matrix, in the form of the polymerized vitreous, necessary to support neovascularization. Thus, the present invention is useful in preventing or reducing the incidence of retinal neovascularization.

Furthermore, many ophthalmic disorders have as a causative component, a destabilization of the blood-retina membrane. This destabilization permits various components (e.g., serum components, lipids, proteins) of the choriocapillaries to enter the vitreal chamber and damage the retinal surface. This destabilization is also a precursor to vascular infiltration of the vitreal chamber, known as neovascularization.

Accordingly, embodiments of the present invention are directed toward the prevention and treatment of various disorders of the mammalian eye which result from damage or pathology to the vascularization of the eye or which result in damage to the blood-retinal barrier. Examples of such diseases include but are not limited to proliferative diabetic retinopathy, age-related macular degeneration, amblyopia, retinitis pigmentosa, macular holes, macular exudates, and cystoid macular edema, and others in which the clinical symptoms of these disorders respond to the hyaluronidase ACS treatment of the present invention.

The following are application examples using the hyaluronidase ACS preparation described hereabove, resulting in improvements of the described ophthalmological disorders. Nevertheless, the present invention contemplates the use of enzymes other than hyaluronidase ACS to induce vitreal liquefaction. Examples of alternative enzymes usable with the present invention include: other glycosaminoglycanase enzymes such as other hyaluronidase preparations, chondroitinase ABC, chondroitinase AC, chondroitinase B, chondroitin 4-sulfatase, chondroitin 6-sulfatase, and B-glucuronidase. Collagenases are also contemplated. Proteases are additionally envisioned.

One of skill in the art wishing to use an enzyme other than hyaluronidase ACS to practice the methods of the present invention would use the teachings herein to select an appropriate enzyme and its dosage. Specifically, the examples discussing enzyme-substrate specificities and non-toxicity studies would be performed with alternative enzyme candidates to establish their effectiveness when used with the present invention. Accordingly, the teachings contained herein are applicable to identifying a substantially non-toxic enzyme that promotes the liquefaction of the vitreous while not causing damage to the retina or other ocular structures.

Hyaluronidase Treatment of Proliferative Diabetic Retinopathy (PDR)

Diabetic retinopathy is the leading cause of blindness in working age Americans. The incidence of retinopathy increases with the time of the disease state, from a level of about 50% manifestation in diabetics with the disease for 7 years to approximately 90% of those with the disease for more than 20 years. It is estimated that PDR affects an estimated 700,000 Americans.

The retinovascular consequences of diabetes essentially consist, in part, of microvascular leakage and capillary nonperfusion resulting from chronic hyperglycemia. Microvascular leakage may in turn result in retinal edema, lipid exudates and intraretinal hemorrhages. Capillary nonperfusion results in the formation of intraretinal microvascular abnormalities (IRMA). These abnormalities are arteriovenous shunts formed to perfuse retinal regions deprived of vascularization by diabetes-mediated arteriole degeneration.

Expression of vascular endothelial growth factor from an hypoxic retina in areas of capillary nonperfusion is thought to result in the development of extraretinal neovascularization. Such neovascularization and its associated fibrous components may spontaneously involute or be complicated by vitreous hemorrhage or traction retinal detachment. Neovascularization may be easily seen on fluorescein angiogram by the profuse leakage of dye from these new vessels since they lack the tight endothelial junctions of the retinal vasculature. Impaired axoplasmic flow in areas of retinal hypoxia result in cotton wool spots.

Proliferative diabetic retinopathy (PDR) requires careful screening of diabetics for early identification and treatment since PDR remains largely asymptomatic in the early stages. Proliferative diabetic retinopathy can be classified into three subgroups: (1) nonproliferative retinopathy; (2) preproliferative retinopathy; (3) proliferative retinopathy. Each classification has certain morphological characteristics. Features of nonproliferative retinopathy include capillary microangiopathy (microvascular obstructions and permeability changes, nonperfusion of capillaries, retinal capillary microaneurysms, basement membrane thickening, and internal microvascular abnormalities (IRMA); intraretinal hemorrhages; exudates; and macular changes. Preproliferative retinopathy is indicated by any or all of the changes described for nonproliferative retinopathy and the following: significant venous beading, cotton-wool exudates, extensive IRMA and extensive retinal ischemia. Proliferative retinopathy is indicated by extraretinal neovascularization and fibrous tissue proliferation, vitreous alterations and hemorrhage, macular disease, and retinal detachment.

The creation of fibrovascular tissue is an especially important complication of PDR since it often will lead to retinal damage mediated by the vitreous. The fibrovascular tissue may form preretinal membranes that create dense adhesions with the posterior hyaloid membrane. These adhesions are responsible for transmitting the forces of vitreous traction to the retina, which may result in retinal detachments.

The vitreous base is normally firmly attached to the adjacent retina and to the outer circumference of the optic nerve head, known as the ring of Martegiani. The attachment of the vitreous to the retina in all other sites between the ring of Martegiani and the vitreous base is much less firm. Neovascularization from the retina leads to the formation of vascular strands extending into the vitreous from the nerve head or elsewhere in the fundus. Contraction of these strands may cause partial or complete retinal detachment.

Retinal detachment at the macula is a major complication of PDR. Most retinal detachments resulting from PDR begin as tractional detachments without holes, but they may become rhegmatogenous by the formation of retinal holes at some later point in the disease. The tractional detachments are caused by abnormal vitreoretinal adhesions or vitreal traction with subsequent shrinkage of the fibrous bands and elevation of the retina.

The present invention contemplates treatment of PDR in the preproliferative and proliferative states using hyaluronidase ACS intravitreal injections. Without being limited to a particular mechanism, it is believed that the effect of intravitreal hyaluronidase ACS injection is to promote the clearance of the liquid phase of the vitreous. The rate of transfer of intravitreally injected tritated water from the mid vitreous to the choroid was significantly increased after depolymerization of vitreous hyaluronic acid by injected hyaluronidase ACS. The present invention capitalizes upon this observation to liquefy the vitreous, for example, in order to promote the clearance of various growth inducing factors and other serum products leaked into the vitreous due to the presence of PDR. It is further contemplated that the hyaluronidase ACS treatment of the present invention may be performed alone or in combination with other treatments of PDR.

EXAMPLE 5

Treatment of Preproliferative Diabetic Retinopathy

In Example 5, a diabetic patient manifesting preproliferative diabetic retinopathy is treated for this complication of diabetes mellitus through the intravitreal injection of hyaluronidase ACS. The purpose of this treatment is to reduce or prevent the development of proliferative diabetic retinopathy manifested by extraretinal neovascularization and fibrous tissue proliferation, vitreous alterations and hemorrhage, macular disease, and retinal detachment.

Once a patient has been diagnosed with diabetes, increased ophthalmic surveillance is performed, given the high percentage of individuals suffering from this disease later developing proliferative diabetic retinopathy (PDR). This increased surveillance should include periodic retinal examinations and fluorescein angiograms to monitor the extent of venous beading, IRMA, and retinal ischemia.

When preproliferative diabetic retinopathy begins reaching the proliferative stage, the hyaluronidase ACS treatment is commenced. This stage is defined as the presence of venous beading in 2 or more quadrants, IRMA in one or more quadrants, and/or microaneurysm and dot hemorrhages in all quadrants. Once these indicia are present, the hyaluronidase ACS treatment method of the present invention is initiated.

The patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Following the preliminary examination, an intravitreal injection of hyaluronidase ACS is given to the patient's affected eye. If both eyes are affected, they may be treated separately. The eye to be treated is injected with 50:1 of 50 IU of the hyaluronidase ACS ophthalmic solution described above intravitreally to promote the depolymerization of vitreous hyaluronic acid, resulting in the liquefaction of the vitreous.

After treatment, the patients' eyes are to be examined on days one (1), two (2), seven (7), fifteen (15), thirty (30) and sixty (60). On each examination day the patient is monitored for vitreous liquefaction. Additionally, the patient is monitored for posterior vitreous detachments using indirect ophthalmoscopy with scleral depression. Finally, the extent of PDR presented by the patient is continuously monitored through periodic retinal examinations and fluorescein angiograms to monitor the extent of venous beading, IRMA, and retinal ischemia.

EXAMPLE 6

Treatment of Proliferative Retinopathy

In this Example, a diabetic patient manifesting proliferative diabetic retinopathy is treated by the intravitreal injection of hyaluronidase ACS. The purpose of this treatment is to reduce the extent of proliferative diabetic retinopathy, to prevent further manifestations of the disease after removal of any extraretinal neovascularized tissue, and to reduce the likelihood of retinal detachment.

A patient presenting proliferative diabetic retinopathy is to receive the hyaluronidase ACS treatment of the present invention in combination with surgical treatment of the neovascularized tissue. The proliferation usually begins with the formation of new vessels with very little fibrous tissue component. They arise from primitive mesenchymal elements that differentiate into vascular endothelial cells. The newly formed vascular channels then undergo fibrous metaplasia; that is, the angiablastic buds are transformed into fibrous tissue.

The new vessels leak fluorescein, so the presence of proliferation is especially noticeable during angiography. The new vessels and fibrous tissue break through the internal limiting membrane and arborize at the interface between the internal limiting membrane and the posterior hyaloid membrane. The fibrovascular tissue may form preretinal membranes that create dense adhesions with the posterior hyaloid membrane. These adhesions are extremely important because they are responsible for transmitting the forces of vitreous traction to the retina during the later stage of vitreous shrinkage.

The proliferative stage of PDR is defined as the presence of three or more of the following characteristics: new vessels, new vessels on or within one disc diameter of the optic nerve, severe new vessels (as defined by one-third disc area neovascularization at the optic nerve or one-half disc area neovascularization at the optic nerve or one-half disc area neovascularization elsewhere), and preretinal or vitreous hemorrhage.

Once diagnosed as entering the proliferative stage, the patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected visual acuity) symptomatology, fundus photography, fluorescein angiography, electroretinography and A-scan measurements.

Following the preliminary examination, an intravitreal injection of hyaluronidase ACS is given to patient's affected eyes. If both eyes are affected, they may be treated separately. The eye is injected with 50:1 of 50 IU of the hyaluronidase ACS ophthalmic solution intravitreally to promote the depolymerization of vitreous hyaluronic acid, resulting in the liquefaction of the vitreous. In addition to depolymerization of the vitreous, the neovascularized tissue is also treated directly to minimize subsequent damage to the retina using panretinal photocoagulation.

Panretinal photocoagulation (PRP) may be used to treat patients presenting PDR in conjunction with the hyaluronidase ACS treatment of the present invention. Panretinal photocoagulation is a form of laser photocoagulation. Currently lasers such as the argon green (614 nm), argon blue-green (488 and 514 nm), krypton red (647 nm), tunable dye, diode and xenon arc lasers, are used for retinal surgery. Laser energy is absorbed predominantly by tissues containing pigment (melanin, xanthophyll, or hemoglobin) producing thermal effects on adjacent structures. Krypton red lasers are the preferred method of treatment, as they are better able to penetrate nuclear sclerotic cataracts and vitreous hemorrhage than the argon lasers, which require more energy to produce equal levels of penetration.

The parameters used during laser retinal surgery may be modified depending on the goal of the photocoagulation. At lower power setting, using longer durations of treatment and producing larger spot sizes, the laser has a coagulative effect on small vessels. Focal laser photocoagulation is used in diabetes to stop leakage of microaneurysms. The laser spot is place directly over the microaneurysm to achieve a slight whitening and closure of the aneurysm. When applied as a grid over an edematous area of retina, the laser may reduce microvascular leakage. At higher energy levels, laser ablation of tissue is possible. Panretinal photocoagulation is thought to be effective by destroying retinal tissue, reducing the amount of ischemic tissue in the eye. Confluent laser spots may be used over a neovascular membrane to obliterate the abnormal vessels.

It should be understood that the present invention does not require a particular order of treatment. In one embodiment, the patient is first treated with hyaluronidase ACS and then laser treatment. In another embodiment the patient is first undergoes laser treatment followed by the hyaluronidase ACS treatment of the present invention.

After treatment, the patients' eyes are to be examined on days one (1), two (2), seven (7), fifteen (15), thirty (30) and sixty (60). On each examination day the patient is monitored for vitreous liquefaction. Additionally, the patient is monitored for posterior vitreous detachments using indirect ophthalmoscopy with scleral depression. Finally, the extent of PDR presented by the patient is continuously monitored through periodic retinal examinations and fluorescein angiograms to monitor the extent of venous beading, IRMA, retinal ischemia, neovascularization, and vitreal hemorrhage. Evidence of new neopolymerization or incomplete depolymerization of the vitreous would warrant a repeat treatment of the patient as described above.

Hyaluronidase Treatment of Age-Related Macular Degeneration

The present invention also contemplates utility in the treatment of age-related macular degeneration (AMD). Age-related macular degeneration consists of a gradual, often bilateral decrease of vision. It is the most common cause of legal blindness in adults. It is probably caused by aging and vascular disease in the choriocapillaries or the afferent retinal vessels. There are basically two morphologic types of AMD: "dry" and "wet".

The underlying abnormality of AMD is the development of involutional changes at the level of Bruch's membrane and the retinal pigment epithelium (RPE). The hallmark lesion of such changes is the druse. Clinically, drusen (the plural form of druse) appear as small, yellow-white deposits at the level of the RPE. Drusen may be categorized as hard, soft or basal laminar drusen.

The present invention is directed both to the treatment and prevention of wet and dry forms of AMD. In the wet form the disease, the condition is thought to affect the choriocapillaries. The choriocapillaries are a component of the choroid which serves to vascularize the globe. The choriocapillaries consists of a rich capillary network that supply most of the nutrition for the pigment epithelium and outer layers of the retina. Damage to the choriocapillaries is thought to result ultimately in neovascular complications, a cause of macular degeneration.

In the dry form, nondisciform macular degeneration results from a partial or total obliteration of the underlying choriocapillaries. Ophthalmoscopically, degeneration of the retinal pigment epithelium and hole formation may be observed. Also, subpigment epithelial deposits of material such as calcium chelates or protinaesous and others may be observed. In dry ADM, secondary retinal changes generally occur gradually, resulting in the gradual loss of visual acuity. Nevertheless, in some percentage of patients, a severe loss of vision results.

The present invention contemplates utility in treating dry ADM and preventing macular degeneration through liquefaction of the vitreous. It is contemplated that the liquefaction of the vitreous would result in an increase in the rate of clearance from the retina of deposited material that later results in macular degeneration.

Wet ADM most frequently results from choriocapillary insufficiency, leading to subsequent subpigment epithelial neovascularization. Neovascularization also is thought to occur as an adaptation of retinal vascularization to inadequate oxygenation as a result of vesicular damage. Neovascularization may also cause several other disorders such as detachment of the pigment epithelium and sensory retina. Typically the disease usually begins after 60 years of age, manifesting in both sexes equally and in patients presenting the disease, bilaterally.

Perhaps the most important complication of age-related macular degeneration is the development of defects in Bruch's membranes of the globe through which new vessels grow. This epithelial neovascularization may result in the production of exudative deposits in and under the retina. The neovascularization may also lead to hemorrhage into the vitreous, which may lead to degeneration of the retina's rods and cones, and cystoid macular edema (discussed below). A macular hole may form which results in irreversible visual loss.

Although affecting only 10% of patients with AMD, neovascular complications of AMD account for the overwhelming majority of cases of severe visual loss. Risk factors include increasing age, soft drusen, nongeographic atrophy, family history, hyperopia, and retinal pigment epithelial detachments. Symptoms of choroidal neovascularization in AMD include metamorphopsia, paracentral scotomas or diminished central vision. Ophthalmoscopic findings include subretinal fluid, blood, exudates, RPE detachment, cystic retinal changes, or the presence of grayish green subretinal neovascular membrane. Fluorescein angiography is often an effective method of diagnosis. During this diagnostic procedure, progressive pooling of the dye in the subretinal space, seen as blurring of the boundaries of the lesion or leakage from undetermined sources are indicators of the disease. Other components of choroidal neovascular membranes as delineated by fluorescein angiography include elevated blocked fluorescence, flat blocked fluorescence, blood, and disciform scar.

The present understanding of neovascular AMD suggests that classic choroidal neovascularization is the lesion component most strongly associated with rapid visual deterioration. Accordingly, treatment of AMD must encompass all neovascular and fibrovascular components of the lesion. At present, treatment is only indicated when classic neovascularization has boundaries that are well demarcated, and photocoagulation has been shown to be beneficial.

In eyes with extrafoveal choroidal neovascularization (>−200 microns from the foveal center), argon laser photocoagulation diminished the incidence of severe visual loss, ($6 lines) at 5 years from 64% to 46%. Recurrent neovascularization developed in one-half of laser-treated eyes, usually in the first year after treatment. Recurrent neovascularization was invariably associated with the development of severe visual loss.

In eyes with juxtafoveal choroidal neovascularization (1 to 199 microns from the foveal center), krypton laser photocoagulation diminished the incidence of severe visual loss from 45% to 31% at 1 year, although the difference between untreated and treated groups was less marked at 5 years.

Laser treatment remains an essential therapeutic method for the treatment of AMD, however, the present invention would augment this method by reducing the reoccurrence of neovascularization.

EXAMPLE 7

Treatment of Age-Related Macular Degeneration

In this Example, a patient manifesting age-related macular degeneration is treated with an intravitreal injection of hyaluronidase ACS. The purpose of this treatment is to reduce or prevent the development of neovascularization, macular disease, and retinal damage.

Once a patient reaches the age of 60, increased ophthalmic surveillance is performed to detect the presence of ADM. This increased surveillance should include periodic retinal examinations and fluorescein angiograms to monitor for the presence of subretinal fluid, blood, exudates, RPE detachment, cystic retinal changes, or the presence of grayish green subretinal neovascular membrane.

When ADM is diagnosed, a regime of hyaluronidase ACS treatment is commenced coupled with or without other treatments such as photocoagulation. As the first step of treatment, the patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Following the preliminary examination, an intravitreal injection of hyaluronidase ACS is given to the patient's affected eye manifesting ADM. If both eyes are affected, they may be treated separately. The eye to be treated is injected with 50:1 of 50 IU of the hyaluronidase ACS ophthalmic solution (described above) intravitreally to promote the depolymerization of vitreous hyaluronic acid, resulting in the liquefaction of the vitreous.

Laser photocoagulation treatment of the hyaluronidase ACS injected eyes may be required. The laser treatment protocol described in Example 5 and 6 should be followed when treating AMD. In an alternative embodiment, photocoagulation treatment occurs before the enzyme treatment of the present invention.

After treatment, the patients' eyes are to be examined on days one (1), two (2), seven (7), fifteen (15), thirty (30) and sixty (60). Because of the possibility of reoccurrence, the patient should return for periodic examinations on a monthly basis thereafter. On each examination day the patient is monitored for vitreous liquefaction. Additionally, the patient is monitored for posterior vitreous detachments using indirect ophthalmoscopy with scleral depression. Finally, the extent of ADM presented by the patient is continuously monitored through periodic retinal examinations and fluorescein angiograms to monitor for the presence of subretinal fluid, blood, exudates, RPE detachment, cystic retinal changes, or the presence of grayish green subretinal neovascular membrane. Additional hyaluronidase ACS and/or laser treatments may be required if indicia of reoccurring neovascularization or are observed.

The following Example demonstrates the efficacy of the present invention, even without the use of photocoagulation.

EXAMPLE 8

Improvement in Symptoms of Macular Degeneration Following Intravitreal Hyaluronidase Injection A greater than seventy-nine (79) year old male human being presented with a history of age-related macular degeneration, and uncorrected vision of 20:400 in his right eye. A single dose of 100 IU of the hyaluronidase ACS was injected intravitreally into his right eye. The other eye remained untreated.

The patient was repeatedly examined post-dose and the vision in his left (untreated) eye remained unchanged, while the vision in his right (treated) eye was observed to improve as follows:

| Time (Post-Dose) | Vision (uncorrected) | Vision (corrected) |
|---|---|---|
| Baseline | 20:400 | none |
| 3 days | cf @ lft. | none |
| 1 wk | 20:400 | none |
| 2 wk | 20:400 | none |
| 4 wk | 20:300 | none | cf denotes finger counting

No adverse effects of the hyaluronidase ACS were observed in this experiment.

Hyaluronidase Treatment of Amblyopia

The term amblyopia is derived from Greek and means dull vision (amblys=dull, ops=eye). Poor vision is caused by abnormal development in visual areas of the brain, which is in turn caused by abnormal visual stimulation during early visual development. The pathology associated with amblyopia is not specific to the eye, rather, it is located in the visual areas of the brain including the lateral geniculate nucleus and the striate cortex. This abnormal development is caused by three mechanisms: (1) blurred retinal image called pattern distortion; (2) cortical suppression, or (3) both cortical suppression plus pattern distortion. The present invention is primarily concerned with pattern distortions caused by media opacity. More specifically, the present invention addresses issues of vitreous opacity.

Amblyopic vision is usually defined as a difference of at least two Snellen lines of visual acuity. Critical to the treatment of amblyopia is early detection and early intervention. The strategy for treating amblyopia caused by vitreous opacity is to provide a clear retinal image by altering the opacity of the vitreous so that clear vision results.

In this Example, a patient manifesting amblyopia resulting from vitreal opacity was treated with an intravitreal injection of hyaluronidase ACS. The purpose of this treatment was to reduce the opacity of the vitreous by increasing the exchange rate of the liquid in the vitreous.

EXAMPLE 9

Improvement in Amblyopia Symptoms Following Intravitreal Hyaluronidase ACS Treatment A forty (40) year old female human being having a history of amblyopia presented with uncorrected vision of 20:400 in her right eye and corrected vision in that eye of 20:200. A single 100 IU dose of the hyaluronidase ACS was injected intravitreally into her right eye. The other eye remained untreated.

The patient was examined repeatedly post-dose and the vision in her left (untreated) eye remained unchanged while the vision in her right (treated) eye was observed to improve as follows:

| Vision (Post-Dose) | Time (uncorrected) | Vision (corrected) |
|---|---|---|
| 4 wk. | 20:200 | 20:70(−1) |
| 8 wk. | 20:200 | 20:60(−2) |
| 12 wk. | 20:200 | 20:60(−1) |
| 52 wk. | 20:200 | 20:60(−1) |

No adverse effects of the hyaluronidase ACS were observed in this patient.

Hyaluronidase Treatment of Retinitis Pigmentosa

Retinitis pigmentosa (RP) is the name given to a group of heritable disorders of progressive retinal degeneration characterized by bilateral nyctalopia constricted visual fields and abnormality of the electroretinogram. Early symptoms include difficulty with dark adaptation and midperipheral visual field loss. As the disease progresses, visual field loss advances, typically leaving a small central field of vision until eventually even central vision is affected. Central acuity may also be affected earlier in the course of disease either by cystoid macular edema, macular atrophy, or development of a posterior subcapsular cataract. RP represents a varied group of diseases whose common thread is the abnormal production of at least one protein in photoreceptor outer segments critical to light transduction.

One clinical result of RP is the destabilization of the blood-retinal barrier of the perifoveal capillaries and the optic nerve head. This destabilization results in leakage of fluorescein dye observed by angiography. In addition to leakage, accumulation of fluid as microcycts in the outer plexiform layer may occur and be observed. These fluid filled cysts may eventually burst, resulting in damage to the retinal layer. The present invention contemplates treating RP related damage to the retina by promoting the accelerated clearance of the tissue fluid accumulating in the microcycts.

EXAMPLE 10

Improvement in Retinitis Pigmentosa Symptoms Following Intravitreal Hyaluronidase A fifty-nine (59) year old male human being presented with a history of retinitis pigmentosa. The uncorrected vision in his left eye was 20:400 and with correction was also 20:400. A single intravitreal injection of 100 IU of the hyaluronidase ACS was administered to the left eye of the patient. The other eye remained untreated.

The patient was examined repeatedly following the dose of hyaluronidase ACS and the vision in the patient's right (untreated) eye remained unchanged, while the vision in the patient's left (treated) eye was observed to improve as follows:

| Time | Intraoccular Pressure | Unaided Vision Acuity | Best Corrected Vision Acuity |
|---|---|---|---|
| Baseline | 17 mm | 20/400 | 20/400 |
| 1 Day Post Treatment | 26 mm | HM†/1 ft | HM/1 ft |
| 1 wk. | — | HM/ 1 ft | HM/1 ft |
| 2 wk. | 14 mm | cf‡@ 3 ft. | cf @3 ft. |
| 3 wk. | 14 mm | 20:300 | 20:300 |
| 4 wk. | 12 mm | 20:200 | 20:80 |
| 8 wk. | 15 mm | 20:80 | 20:40 |
| 9 wk. | 15 mm | 20:60 | 20:40 |
| 10 wk. | 18 mm | 20:80 | 20:40 |

†HM denotes "hand movement"
‡cf denotes "finger counting"

The study results demonstrate that there were significant improvements in the visual performance of the subject, both with respect to Unaided Visual Acuity (improving from 20:400 to 20:80) and Best Corrected Visual Acuity (improving from 20:400 to 20:40). Also, while changes in the intraoccular pressure of the subject during the treatment period were observed, the intraoccular pressure appeared to return to baseline levels approximately two weeks after the time of injection. Although these results are from a single patient, they appear sufficiently promising to warrant further studies.

Hyaluronidase Treatment of Macular Holes

A rupture or bursting open of the macula is known as a macular hole. Interestingly, this condition usually occurs in women in their sixth through eighth decades, or after trauma such as lightening injury, solar injury, scleral buckling, or in staphylomatous eyes. Symptoms include metamorphopsia and diminished visual acuity.

Macular hole formation is thought to result from tangential traction across the retinal surface induced by the posterior cortical vitreous with involvement of fluid movement within a posterior vitreous syneresis cavity. The posterior vitreous syneresis cavity is present in the vast majority of patients presenting macular holes. It is thought that as the posterior vitreal gel retreats from the retinal surface, the resulting gap between the two surfaces creates an area wherein movement of the vitreous humor may negatively interact with the retinal surface. The tangential movement of the vitreous humor within the space of the posterior vitreous syneresis cavity is thought to promote tears of the retinal membrane, resulting in the creation of macular holes.

The present invention contemplates the use of hyaluronidase ACS to depolymerize the vitreous so as to eliminate the conditions which result in macular hole formation. Upon depolymerization of the vitreous, the posterior vitreous syneresis cavity is eliminated as a result of hyaluronidase ACS-mediated reorganization of the vitreous. The elimination of this cavity permits the fluid between the vitreous and the retina to move freely about the vitreal chamber, dispersing any harmful forces that would have otherwise have been directed against the retinal surface.

The following Example discusses the treatment of a patient presenting the early symptoms of macular hole formation.

EXAMPLE 11

Treatment of Macular Holes

A patient presenting the early signs of macular hole formation is treated with an intravitreal injection of hyaluronidase ACS. The patient to be treated presents the various signs of premacular hole formation. These include loss of the foveal depression associated with a yellow foveal spot or ring. The fovea has begun to thin in the region of hole formation and the lesion may obtain a reddish appearance. Fluorescein angiography at this stage may appear normal or show faint hyperfluorescence. The appearance of an eccentric full thickness dehiscence denotes an advanced early stage of the disease. Upon observance of these symptoms hyaluronidase ACS treatment is commenced.

The hyaluronidase ACS treatment of the present invention is commenced when the formation of a macular hole is diagnosed. The patient is to receive a full ophthalmic examination to establish a baseline of ocular health. The ophthalmic examination included indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Following the preliminary examination, an intravitreal injection of hyaluronidase ACS is given to the patient's affected eye. If both eyes are affected, they may be treated separately. The eye to be treated is injected with 50:1 of 50 IU of the hyaluronidase ACS ophthalmic solution described above intravitreally to promote the depolymerization of vitreous hyaluronic acid, resulting in the liquefaction of the vitreous.

After treatment, the patients' eyes are to be examined on days one (1), two (2), seven (7), fifteen (15), thirty (30) and sixty (60). On each examination day the patient is monitored for vitreous liquefaction. Fluorescein angiography, considered a particularly effect method of monitoring the course of the treatment, is also performed. Additionally, the patient is monitored for posterior vitreous detachments using indirect ophthalmoscopy with scleral depression.

Hyaluronidase Treatment of Macular Exudates

Macular exudates are material that penetrates the blood-retina barrier and seeps through the macula into the vitreal chamber. There are two kinds, soft exudates and hard exudates. The soft exudates are actually not exudates but clusters of ganglion cell axons in the nerve fiber layer that have undergone a bulbous dilation at a site of ischemic damage or infarction. Hard exudates are commonly exuded as a result of microvascular changes in background retinopathy. Hard exudates appear yellow and waxy are often deposited in a circular fashion about the macula. They consists of lipid and proteinaceous material derived from the exudation of serum components from leaking vessels or from the lipid products of degenerating neural elements within the retina. Adsorption of hard exudates is primarily mediated by macrophagic resorption, however, the rate of this process may be slow since exudation often occurs in the outer plexiform layer within the avascular zone of the retina. The present invention is particularly useful in reducing the extent of exudative accumulation resulting from the destabilization of the retinal membrane since hyaluronidase ACS depolymerization of the vitreous promotes an increased turn-over rate of the aqueous components of the vitreous.

EXAMPLE 12

Treatment of Macular Exudates

A patient presenting macular exudates is treated with hyaluronidase ACS injection method of the present invention. The patient is to receive a full ophthalmic examination to establish a baseline of ocular health. The ophthalmic examination included indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements.

Following the preliminary examination, an intravitreal injection of hyaluronidase ACS is given to the patient's affected eye. If both eyes are affected, they may be treated separately. The eye to be treated is injected with 50:1 of 50 IU of the hyaluronidase ACS ophthalmic solution described above intravitreally to promote the depolymerization of vitreous hyaluronic acid, resulting in the liquefaction of the vitreous.

After treatment, the patients' eyes are to be examined on days one (1), two (2), seven (7), fifteen (15), thirty (30) and sixty (60). On each examination day the patient is monitored for vitreous liquefaction. Fluorescein angiography, considered a particularly effect method of monitoring the course of the treatment, is also performed. Additionally, the patient is monitored for posterior vitreous detachments using indirect ophthalmoscopy with scleral depression.

Treatment of Cystoid Macular Edema

Cystoid macular edema is a common ocular abnormality resulting form a diverse group of etiologies. Most the causes of this condition stem from a disturbance of the blood-retinal barrier of the perifoveal capillaries and the optic nerve head that result in fluid leakage which accumulates in microcysts of the outer plexiform layer. This region is a relatively thin and under vascularized area of the retina. Clinically, a cystoid macular edema produces a honey-comb appearance when examined with fluorescein angiography. As the edema progresses, the outer plexiform layer may rupture, producing a lamellar hole. The hole may be confined to the inner layer of the retina or it may eventually progress to a complete macular hole.

The present invention contemplates the treatment of cystoid macular edema and the prevention of macular hole formation through the hyaluronidase ACS-mediated depolymerization of the vitreous.

EXAMPLE 13

Treatment of Macular Exudates

A patient presenting the indicia of cystoid macular edema is treated with an intravitreal hyaluronidase ACS injection as described in Examples 11 and 12.

It will be appreciated by those skilled in the art that the invention has been described hereabove with reference to certain presently preferred embodiments and examples only, and no effort has been made to exhaustively describe all embodiments in which the invention may take physical form or be practiced. Indeed, various modifications may be made to the specific embodiments and examples described here above, without departing from the intended spirit and scope of the present invention. Accordingly, it is intended that all such reasonable modifications to the above be included within the scope of the following claims.

What is claimed is:

1. A method for inducing liquefaction of a vitreous humor to treat a disorder of a mammalian eye, said method comprising contacting with said vitreous humor of said mammalian eye an amount of hyaluronidase effective to liquefy said vitreous humor whereby said disorder is treated, wherein said hyaluronidase is defined as being free of thimerosal, and essentially devoid of hyaluronidase molecular weight fractions above 100,000, between 50,000 and 60,000, and below 20,000 as determined by 4–20% Gradient SDS PAGE electrophoresis, and wherein said hyaluronidase is defined as causing hydrolysis of the endo-N-acetyl hexosaminic bonds of hyaluronic acid.

2. The method of claim 1, wherein said method is carried out for the purpose of treating proliferative diabetic retinopathy.

3. The method of claim 1, where in said method is carried out for the purpose of treating age-related macular degeneration.

4. The method of claim 1, wherein said method is carried out for the purpose of treating amblyopia.

5. The method of claim 1, wherein said method is carried out for the purpose of treating retinitis pigmentosa.

6. The method of claim 1, wherein said method is carried out for the purpose of treating macular holes.

7. The method of claim 1, wherein said method is carried out for the purpose of treating macular exudates.

8. The method of claim 1, wherein said method is carried out for the purpose of treating cystoid macular edema.

9. The method of claim 1, wherein said hyaluronidase is in a liquid solution, and wherein the step of contacting of said enzyme with the vitreous humor comprises:
    injecting said liquid solution into the vitreous humor.

10. The method of claim 1, wherein said hyaluronidase is contacted with the vitreous humor at a dose of 5–200 International Units.

11. The method of claim 1, wherein said hyaluronidase is contacted with the vitreous humor at a dose of 1 International Unit.

12. The method of claim 1, wherein said hyaluronidase is administered in multiple doses.

13. The method of claim 12, wherein a single intravitreal injection has an injectate volume of less than 100:1.

14. The method of claim 1, wherein said hyaluronidase is prepared in a solution for injection and which has a formulation:
    said hyaluronidase up to 8000 IU;
    lactose at 5.0–130.0 mg; and
    phosphate at 0.01–100.0 mmoles.

15. The method of claim 1, wherein said hyaluronidase is prepared in a solution for injection and which has a formulation:
    said hyaluronidase at 6500 IU;
    lactose at 5.0 mg; and
    phosphate at 0.02 mmoles.

16. The method of claim 1, wherein said hyaluronidase is prepared in a solution for injection and which has a formulation:
    said hyaluronidase at 500–1000 IU;
    lactose at 5.0–10.0 mg; and
    phosphate at 0.01–10.0 mmoles.

17. The method of claim 1, wherein said liquefaction achieves posterior vitreal detachment (PVD).

18. The method of claim 1, wherein the hyaluronidase is ovine testicular hyaluronidase.

19. The method of any of claims 1–7, wherein prior to liquefaction said vitreous humor is free of hemorrhagic blood that permits viewing of a retina of said mammalian eye.

20. The method of any of claims 1–7, wherein said contacting step is practiced in the absence of vitrectomy.

* * * * *